US008951989B2

(12) United States Patent
Wagman

(10) Patent No.: US 8,951,989 B2
(45) Date of Patent: Feb. 10, 2015

(54) HYDROGEL TISSUE ADHESIVE HAVING REDUCED DEGRADATION TIME

(75) Inventor: Mark E. Wagman, Wilmington, DE (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 584 days.

(21) Appl. No.: 13/263,364

(22) PCT Filed: Apr. 9, 2010

(86) PCT No.: PCT/US2010/030474
§ 371 (c)(1),
(2), (4) Date: Oct. 7, 2011

(87) PCT Pub. No.: WO2010/118284
PCT Pub. Date: Oct. 14, 2010

(65) Prior Publication Data
US 2012/0035129 A1  Feb. 9, 2012

Related U.S. Application Data

(60) Provisional application No. 61/167,877, filed on Apr. 9, 2009, provisional application No. 61/167,881, filed on Apr. 9, 2009, provisional application No. 61/167,879, filed on Apr. 9, 2009.

(51) Int. Cl.
| | | |
|---|---|---|
| *A61K 31/70* | (2006.01) | |
| *A61K 31/715* | (2006.01) | |
| *C08L 5/08* | (2006.01) | |
| *C08L 5/12* | (2006.01) | |
| *C08L 71/02* | (2006.01) | |
| *A61K 31/717* | (2006.01) | |
| *A61K 31/718* | (2006.01) | |
| *A61K 31/719* | (2006.01) | |
| *A61K 31/721* | (2006.01) | |
| *A61L 24/00* | (2006.01) | |
| *A61L 24/04* | (2006.01) | |
| *A61L 31/04* | (2006.01) | |
| *A61L 31/14* | (2006.01) | |
| *C08L 1/04* | (2006.01) | |
| *C08L 3/10* | (2006.01) | |
| *C08L 5/02* | (2006.01) | |

(52) U.S. Cl.
CPC ......... *A61L 24/0031* (2013.01); *A61L 24/0042* (2013.01); *A61L 24/043* (2013.01); *A61L 31/041* (2013.01); *A61L 31/145* (2013.01); *A61L 31/148* (2013.01); *C08L 1/04* (2013.01); *C08L 3/10* (2013.01); *C08L 5/02* (2013.01); *C08L 5/08* (2013.01); *C08L 5/12* (2013.01); *C08L 71/02* (2013.01)
USPC .................. 514/54; 514/53; 514/57; 514/59; 514/60

(58) Field of Classification Search
CPC ... A61K 31/70; A61K 31/715; A61K 31/717; A61K 31/718; A61K 31/719; A61K 31/721
USPC .................................... 514/53, 54, 57, 59, 60
See application file for complete search history.

(56) References Cited

U.S. PATENT DOCUMENTS

| | | |
|---|---|---|
| 4,542,176 A | 9/1985 | Graham |
| 4,584,188 A | 4/1986 | Graham |
| 4,703,116 A | 10/1987 | Solarek et al. |
| 4,731,162 A | 3/1988 | Solarek et al. |
| 4,741,804 A | 5/1988 | Solarek et al. |
| 4,749,800 A | 6/1988 | Jobe et al. |
| 4,766,245 A | 8/1988 | Larkin et al. |
| 4,839,449 A | 6/1989 | Billmers et al. |
| 4,909,251 A | 3/1990 | Seelich |
| 4,911,926 A | 3/1990 | Henry et al. |
| 4,929,670 A | 5/1990 | Billmers et al. |
| 5,011,918 A | 4/1991 | Bilimers et al. |
| 5,049,634 A | 9/1991 | Tsai et al. |
| 5,092,883 A | 3/1992 | Eppley et al. |
| 5,116,824 A | 5/1992 | Miyata et al. |
| 5,162,430 A | 11/1992 | Rhee et al. |
| 5,196,441 A | 3/1993 | Kunisch et al. |
| 5,217,485 A | 6/1993 | Liu et al. |
| 5,275,838 A | 1/1994 | Merrill |
| 5,283,339 A | 2/1994 | Arnold et al. |

(Continued)

FOREIGN PATENT DOCUMENTS

| | | |
|---|---|---|
| EP | 0961783 | 1/2007 |
| JP | 1982-102932 | 6/1982 |

(Continued)

OTHER PUBLICATIONS

BASF Corp, Technical Bulletin, Pluronic F108 Block Copolymer Surfactant, (2004), 1 page.
Ahmad, Shavej, et al., "Dextran and 5-aminosalicylic Acid (5-ASA) Conjugates: Synthesis, Characterisation and Enzymic Hydrolysis", Carbohydrate Research, vol. 341, 2006, pp. 2694-2701.
Cortesi, Rita, et al., "Dextran Cross-Linked Gelatin Microspheres as a Drug Delivery System", European Journal of Pharmaceutics and Biopharmaceutics, vol. 47, 1999, pp. 153-160.
Gill, Inderbir S., et al., "Improved Hemostasis During Laparoscopic Partial Nephrectomy Using Gelatin Matrix Thrombin Sealant", Adult Urology, vol. 64, No. 3, 2005, pp. 463-466.

(Continued)

*Primary Examiner* — Patrick Lewis
*Assistant Examiner* — Everett White
(74) *Attorney, Agent, or Firm* — McCarter & English

(57) ABSTRACT

A hydrogel tissue adhesive having decreased degradation time is described. The hydrogel tissue adhesive is formed by reacting an oxidized polysaccharide with a water-dispersible, multi-arm polyether amine in the presence of an oligomer additive, which promotes the degradation of the hydrogel. The hydrogel may be useful as a tissue adhesive or sealant for medical applications, such as a hemostat sealant or to prevent undesired tissue-to-tissue adhesions resulting from trauma or surgery.

20 Claims, No Drawings

(56) References Cited

U.S. PATENT DOCUMENTS

| | | | |
|---|---|---|---|
| 5,292,802 A | 3/1994 | Rhee et al. |
| 5,308,889 A | 5/1994 | Rhee et al. |
| 5,324,775 A | 6/1994 | Rhee et al. |
| 5,328,995 A | 7/1994 | Schaulin et al. |
| 5,451,398 A | 9/1995 | Vigh |
| 5,502,042 A | 3/1996 | Gruskin et al. |
| 5,505,952 A | 4/1996 | Jiang et al. |
| 5,514,379 A | 5/1996 | Weissleder et al. |
| 5,567,685 A | 10/1996 | Linden et al. |
| 5,643,575 A | 7/1997 | Martinez et al. |
| 5,733,563 A | 3/1998 | Fortier |
| 5,776,706 A | 7/1998 | Siiman et al. |
| 5,830,986 A | 11/1998 | Merrill et al. |
| 5,840,698 A | 11/1998 | Campbell et al. |
| 5,843,865 A | 12/1998 | Del Corral et al. |
| 5,874,500 A | 2/1999 | Rhee et al. |
| 5,990,237 A | 11/1999 | Bentley et al. |
| 6,051,648 A | 4/2000 | Rhee et al. |
| 6,121,375 A | 9/2000 | Eknoian |
| 6,150,472 A | 11/2000 | Engbers |
| 6,165,488 A | 12/2000 | Tardy et al. |
| 6,166,130 A | 12/2000 | Rhee et al. |
| 6,323,278 B2 | 11/2001 | Rhee et al. |
| 6,391,939 B2 | 5/2002 | Tayot et al. |
| 6,410,519 B1 | 6/2002 | Gruskin et al. |
| 6,458,147 B1 | 10/2002 | Cruise et al. |
| 6,458,889 B1 | 10/2002 | Trollsas et al. |
| 6,465,694 B1 | 10/2002 | Baudys et al. |
| 6,514,534 B1 | 2/2003 | Sawhney |
| 6,534,591 B2 | 3/2003 | Rhee et al. |
| 6,602,952 B1 | 8/2003 | Bentley et al. |
| 6,620,125 B1 | 9/2003 | Redl |
| 6,689,399 B1 | 2/2004 | Dickson |
| 6,696,089 B2 | 2/2004 | Kabanov et al. |
| 6,703,047 B2 | 3/2004 | Sawhney et al. |
| 6,756,518 B2 | 6/2004 | Gruskin et al. |
| 6,800,278 B1 | 10/2004 | Perrault et al. |
| 6,833,408 B2 | 12/2004 | Sehl et al. |
| 6,858,736 B2 | 2/2005 | Nho et al. |
| 6,896,725 B2 | 5/2005 | Thornton et al. |
| 6,958,325 B2 | 10/2005 | Domb |
| 7,001,891 B1 | 2/2006 | Domb |
| 7,196,180 B2 | 3/2007 | Aeschlimann et al. |
| 7,217,845 B2 | 5/2007 | Rosen et al. |
| 7,255,999 B2 | 8/2007 | Singh et al. |
| 7,459,185 B2 | 12/2008 | Gutowski et al. |
| 7,780,980 B2 | 8/2010 | Sawhney |
| 7,834,065 B2 | 11/2010 | Nakajima et al. |
| 7,837,986 B2 * | 11/2010 | Chenault | 424/78.2 |
| 7,854,923 B2 | 12/2010 | Chen et al. |
| 7,960,498 B2 | 6/2011 | Chenault et al. |
| 8,257,685 B2 | 9/2012 | Smyth et al. |
| 8,263,582 B2 * | 9/2012 | Stergis et al. | 514/179 |
| 8,426,492 B2 | 4/2013 | Lu |
| 8,466,327 B2 | 6/2013 | Arthur |
| 8,551,136 B2 | 10/2013 | Lu |
| 8,580,950 B2 | 11/2013 | Lu et al. |
| 8,580,951 B2 | 11/2013 | Lu et al. |
| 2002/0151520 A1 | 10/2002 | Gruskin |
| 2003/0022216 A1 | 1/2003 | Mao et al. |
| 2003/0027788 A1 | 2/2003 | Singh et al. |
| 2003/0064502 A1 | 4/2003 | Illman et al. |
| 2003/0087111 A1 | 5/2003 | Hubbell et al. |
| 2003/0108511 A1 | 6/2003 | Sawhney |
| 2003/0119985 A1 | 6/2003 | Sehl et al. |
| 2004/0086479 A1 | 5/2004 | Grinstaff et al. |
| 2004/0096507 A1 | 5/2004 | Kwang et al. |
| 2004/0225097 A1 | 11/2004 | Nho et al. |
| 2004/0235708 A1 | 11/2004 | Rhee et al. |
| 2005/0002893 A1 | 1/2005 | Goldmann |
| 2005/0020805 A1 | 1/2005 | Sunkara et al. |
| 2005/0288684 A1 | 12/2005 | Aronson et al. |
| 2006/0078536 A1 | 4/2006 | Kodokian et al. |
| 2006/0110427 A1 | 5/2006 | Molock et al. |
| 2006/0115531 A1 | 6/2006 | Chenault |
| 2006/0292030 A1 | 12/2006 | Odermatt et al. |
| 2007/0031467 A1 | 2/2007 | Abrahams et al. |
| 2007/0048251 A1 | 3/2007 | Arthur |
| 2007/0249870 A1 | 10/2007 | Chenault |
| 2008/0051323 A1 | 2/2008 | Kosak |
| 2008/0220047 A1 | 9/2008 | Sawhney et al. |
| 2008/0319101 A1 | 12/2008 | Nakajima et al. |
| 2009/0035249 A1 | 2/2009 | Bhatia et al. |
| 2009/0054535 A1 | 2/2009 | Figuly et al. |
| 2010/0015231 A1 | 1/2010 | Lu |
| 2010/0086678 A1 | 4/2010 | Arthur et al. |
| 2010/0112063 A1 | 5/2010 | Figuly et al. |
| 2010/0160960 A1 | 6/2010 | Wagman et al. |
| 2010/0255101 A1 | 10/2010 | Lu |
| 2011/0224724 A1 | 9/2011 | Lu et al. |
| 2011/0250257 A1 | 10/2011 | Arthur et al. |
| 2011/0269916 A1 | 11/2011 | Chenault et al. |
| 2012/0035129 A1 | 2/2012 | Wagman |
| 2012/0094955 A1 | 4/2012 | Wagman |
| 2012/0148523 A1 | 6/2012 | Lu et al. |

FOREIGN PATENT DOCUMENTS

| | | |
|---|---|---|
| JP | 1988-11167 | 1/1988 |
| WO | WO 87/00836 | 2/1987 |
| WO | WO 90/10441 | 9/1990 |
| WO | WO 91/15368 | 10/1991 |
| WO | WO 97/30103 | 8/1997 |
| WO | WO 99/01143 | 1/1999 |
| WO | WO 00/69925 | 11/2000 |
| WO | WO 01/49268 | 7/2001 |
| WO | WO 01/72280 | 10/2001 |
| WO | WO 01/87986 | 11/2001 |
| WO | WO 02/102864 | 12/2002 |
| WO | WO 03/020818 | 3/2003 |
| WO | WO 03/097759 | 11/2003 |
| WO | WO 2006/031358 | 3/2006 |
| WO | WO 2006/042161 | 4/2006 |
| WO | WO 2006/080523 | 8/2006 |
| WO | WO 2006/086510 | 8/2006 |
| WO | WO 2008/005207 | 1/2008 |
| WO | WO 2008/066787 | 6/2008 |
| WO | WO 2009/064977 | 5/2009 |
| WO | WO 2010/111570 | 9/2010 |
| WO | WO 2010/118284 | 10/2010 |

OTHER PUBLICATIONS

Yao, Zhong, et al., "A Series of Novel Chitosan Derivatives: Synthesis, Characterization and Micellar Solubilization of Paclitaxel", Carbohydrate Polymers, 2007, vol. 68, pp. 781-792.

Balakrishnan, Biji, et al., "Self-cross-linking biopolymers as injectable in situ forming biodegradable scaffolds", Biomaterials, 2005, vol. 26, pp. 3941-3951.

Rebizak, Richard, et al., "Macromolecular contrast agents for magnetic resonance imaging influence of polymer content in ligand on the paramagnetic properties", European Journal of Pharmaceutical Sciences, 1999, vol. 7, pp. 243-248.

Zalipsky, Samuel, et al., "Hydrazide Derivatives of Poly(ethylene glycol) and Their Bioconjugates", ACS Symposium Series; American Chemical Society, 1997, pp. 318-341.

Sgouras, D., et al., "Method for the evaluation of biocompatibility of soluble synthetic polymers which have potential for biomedical use: 1—Use of the tetrazolium-based colorimetric assay (MTT) as a preliminary screen for evaluation of in vitro cytotoxicity", Journal of Materials Sciences: Materials in Medicine, 1990, vol. 1, pp. 61-68.

Thome, J., et al., "Ultrathin Antibacterial Polyammonium Coatings on Polymer Surfaces"; Surface and Coatings Technology, 174-175, 2003, pp. 584-587.

Harris, J. Milton, "Laboratory Synthesis of Polyethylene Glycol Derivatives", JMS-Rev., Macromol. Chem. Phys., C25 (3), 1985, pp. 325-373.

Harris, J. Milton, et al., "Synthesis of New Poly(Ethylene Glycol) Derivatives", PolyEthylene Glycol Chemistry: Biotechnical and Biomedical Applications, edited by Milton J. Harris, Plenum Press: New York, 1992, pp. 371-381.

Chen, Nicole, et al., "Mechanisms of Aldehyde-Containing Paper Wet-Strength Resins", Industrial & Engineering Chemistry Research, vol. 41, No. 22, 2002, pp. 5366-5371.

(56) References Cited

OTHER PUBLICATIONS

Callant, Dominique, et al., "A New Approach to Dextran Derivatives with Pendent Aldehyde Groups", Reactive Polymers, vol. 8, 1988, pp. 129-136.
Hollander, Andreas, et al., "Polymer Surface Chemistry for Biologically Active Materials", Applied Surface Science, vol. 235, 2004, pp. 145-150.
Stone, H. Harlan, et al., "Antibiotic Prophylaxis in Gastric, Biliary and Colonic Surgery", Ann. Surg; Oct. 1976, pp. 443-450.
Fishman, Alexander, et al., "Synthesis and Investigation of Novel Branched PEG-Based Soluble Polymer Supports", The Journal of Organic Chemistry, vol. 68, 2003, pp. 9843-9846.
Newkome, George R., "Improved Synthesis of an Ethereal Tetraamine Core for Dendrimer Construction", The Journal of Organic Chemistry, vol. 67, 2002, pp. 3957-3960.
Halabi, A., et al., "Synthesis and characterization of a Novel Dendritic Acrylic Monomer", The Journal of Organic Chemistry, vol. 65, 2000, pp. 9210-9213.
Harris, J. Milton, et al., "Synthesis and Characterization of Poly(ethylene Glycol) Derivatives", Journal of Polymer Science: 1984, Polymer Chemistry Edition, vol. 22, 1984, pp. 341-352.
Merrill, Edward W., "Poly(ethylene oxide) Star Molecules: Synthesis, Characterization, and Applications in Medicine and Biology", Journal of Biomaterials Science Polymer Edition, vol. 5, No. 1/2, 1993, pp. 1-11.
Zhao, Xuan, et al., "Novel Degradable Poly(ethylene glycol) Esters for Drug Delivery", Poly(ethylene glycol) Chemistry and Biological Applications, Oxford University Press, 1998, Chapter 28, pp. 458-472.
Azzam, Tony, et al., "Cationic Polysaccharides for Gene Delivery", Macromolecules, vol. 35, No. 27, 2002, pp. 9947-9953.
Nagasaki, Yukio, et al., "Formyl-Ended Heterobifunctional Poly(ethylene oxide): Synthesis of Poly(ethylene oxide) with a Formyl Group at One End and a Hydroxyl Group at the Other End", Bioconjugate Chemistry, vol. 6, No. 2, 1995, pp. 231-233.
Greenwald, Richard B., et al., "Drug Delivery Systems Employing 1,4- or 1,6-Elimination: Poly(ethylene glycol) Prodrugs of Amine-Containing Compounds", Journal of Medicinal Chemistry, vol. 42, No. 18, 1999, pp. 3657-3667.
Zalipsky, Samuel, et al., "Preparation and Applications of Polyethylene Glycol—Polystyrene Graft Resin Supports for Solid-Phase Peptide Synthesis", Reactive Polymers, vol. 22, 1994, pp. 243-258.
Lara, V.S., et al., "Dentin-Induced in Vivo Inflammatory Response and in Vitro Activation of Murine Macrophages", Journal of Dental Research, vol. 82, No. 6, 2003, pp. 460-465.
Atassi, M.Z., "Immunochemistry of Proteins", vol. 1, Plenum Press, New York, 1977, pp. 59-60.
Sweeney, Thomas, et al., "Intestinal Anastomoses Detected with a Photopolymerized Hydrogel", Surgery, vol. 131, No. 2, Feb. 2002, pp. 185-189.
Kim, Jae Chan, et al., "Evaluation of Tissue Adhesives in Closure of Scleral Tunnel Incisions", Journal of Cataract & Refractive Surgery, vol. 21, May 1995, pp. 320-325.
Sarayba, Melvin A., et al., "Inflow of Ocular Surface Fluid Through Clear Corneal Cataract Incisions: A Laboratory Model", American Journal of Ophthalmology, vol. 138, No. 2, Aug. 2004, pp. 206-210.
Buckmann, Andreas F., et al., "Functionalization of Poly(ethylene glycol) and Monomethoxy-Poly(ethylene glycol)", Makromolecular Chemistry, vol. 182, 1981, pp. 1379-1384.
Bruce, J., et al., "Systematic Review of the Definition and Measurement of Anastomotic Leak after Gastrointestinal Surgery", British Journal of Surgery, vol. 88, 2001, pp. 1157-1168.
Mo, Xiumei, et al "Soft Tissue Adhesive Composed of Modified Gelatin and Polysaccharides", Journal of Biomaterials Science Polymer Edition, vol. 11, No. 4, 2000, pp. 341-351.
Hofreiter, B.T., et al., "Rapid Estimation of Dialdehyde Content of Periodate Oxystarch through Quantitative Alkali Consumption", Analytical Chemistry, vol. 27, No. 12, Dec. 1955, pp. 1930-1931.
Zhao, Huiru, et al., "Determination of Degree of Substitution of Formyl Groups in Polyaldehyde Dextran by the Hydroxylamine Hydrochloride Method", Pharmaceutical Research, vol. 8, No. 3, 1991, pp. 400-402.
Kurisawa, Motoichi, et al., "Double-Stimuli-Responsive Degradation of Hydrogels Consisting of Oligopeptide-Terminated Poly(ethylene glycol) and Dextran with an Interpenetrating Polymer Network", Journal of Biomaterials Science Polymer Edition, vol. 8, No. 9, 1997, pp. 691-708.
Pfannemuller, B., et al., "Chemical Modification of the Surface of the Starch Granules", Starch/Starke, vol. 95, No. 9, 1983, pp. 298-303.

* cited by examiner

HYDROGEL TISSUE ADHESIVE HAVING REDUCED DEGRADATION TIME

CROSS-REFERENCE TO RELATED APPLICATIONS

This application is a national stage application filed under 35 U.S.C. §371 of PCT/US10/30473, filed Apr. 9, 2010 and claims priority under 35 U.S.C. §119 from U.S. Provisional Application Ser. Nos. 61/167,877, 61/167,881, and 61/167,879, all of which were filed on Apr. 9, 2009, and all of which are incorporated herein by reference.

FIELD OF THE INVENTION

The invention relates to the field of medical adhesives. More to specifically, the invention relates to a hydrogel tissue adhesive formed by reacting an oxidized polysaccharide with a water-dispersible, multi-arm polyether amine wherein the hydrogel comprises an oligomer additive which reduces the degradation time of the hydrogel.

BACKGROUND OF THE INVENTION

Tissue adhesives have many potential medical applications, including wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, fibrin-based adhesives do not bond covalently to the underlying tissue.

Several types of hydrogel tissue adhesives have been developed, which have improved adhesive and cohesive properties and are nontoxic (see for example Sehl et al., U.S. Patent Application Publication No. 2003/0119985, and Goldmann, U.S. Patent Application Publication No. 2005/0002893). These hydrogels are generally formed by reacting a component having nucleophilic groups with a component having electrophilic groups, which are capable of reacting with the nucleophilic groups of the first component, to form a crosslinked network via covalent bonding. However, these hydrogels typically swell, dissolve away too quickly, or lack sufficient adhesion or mechanical strength, thereby decreasing their effectiveness as surgical adhesives.

Kodokian et al. (copending and commonly owned U.S. Patent Application Publication No. 2006/0078536) describe hydrogel tissue adhesives formed by reacting an oxidized polysaccharide with a water-dispersible, multi-arm polyether amine. These adhesives provide improved adhesion and cohesion properties, crosslink readily at body temperature, maintain dimensional stability initially, do not degrade rapidly, and are nontoxic to cells and non-inflammatory to tissue. However, for certain applications such as use as a hemostat sealant or to prevent undesired tissue-to-tissue adhesions resulting from trauma or surgery, tissue adhesives that are fast gelling, have good adhesive and cohesive strength, and degrade more rapidly are needed. It can be difficult to decrease the degradation time of the hydrogel without an undesired increase in the gelation time.

Figuly et al. (copending and commonly owned U.S. patent application Ser. No. 12/145,737) describe a method for extending the gelation time of an oxidized polysaccharide to react with a water-dispersible, multi-arm polyether amine to form a hydrogel. The method also decreases the degradation time of the hydrogel. The method utilizes a chemical additive that reacts with the functional groups of the oxidized polysaccharide or the water-dispersible, multi-arm polyether amine, thereby reducing the number of groups available for crosslinking.

Therefore, the need exists for a hydrogel tissue adhesive that is fast gelling, has good adhesive and cohesive strength, and degrades more rapidly than conventional hydrogel adhesives.

SUMMARY OF THE INVENTION

The present invention addresses the above need by providing a hydrogel tissue adhesive formed by reacting an oxidized polysaccharide with a water-dispersible, multi-arm polyether amine wherein the hydrogel comprises an oligomer additive which reduces the degradation time of the hydrogel.

Accordingly, in one embodiment the invention provides a kit comprising:
a) at least one oxidized polysaccharide containing aldehyde groups, said oxidized polysaccharide having a weight-average molecular weight of about 1,000 to about 1,000,000 Daltons and having an equivalent weight per aldehyde group of about 65 to about 1500 Daltons;
b) at least one water-dispersible, multi-arm polyether amine wherein at least three of the arms are terminated by at least one primary amine group, said multi-arm polyether amine having a number-average molecular weight of about 450 to about 200,000 Daltons; and
c) at least one oligomer of the formula:

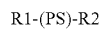

R1-(PS)-R2 wherein:
(i) PS is a linear polymeric segment comprising ethylene oxide monomers or a combination of ethylene oxide and propylene oxide monomers, wherein said ethylene oxide monomers comprise at least about 50 weight percent of said polymeric segment;
(ii) R1 is at least one nucleophilic group capable of reacting with aldehyde groups to form at least one reversible covalent bond;
(iii) R2 is at least one functional group which is not capable of reacting with an aldehyde, a primary amine, a secondary amine, or R1 to form a covalent bond, such that said oligomer does not induce gelation when mixed in an aqueous medium with either (a) alone or (b) alone;
(iv) said oligomer has a weight-average molecular weight of about 200 to about 10,000 Daltons; and
(v) said oligomer is water soluble.

In another embodiment, the invention provides a dried hydrogel formed by a process comprising the steps of:
a) combining in a solvent (i) at least one oxidized polysaccharide containing aldehyde groups, said oxidized polysaccharide having a weight-average molecular weight of about 1,000 to about 1,000,000 Daltons and having an equivalent weight per aldehyde group of about 65 to about 1500 Daltons with (ii) at least one water-dispersible, multi-arm polyether amine, wherein at least three of the arms are terminated by at least one primary amine group, said multi-arm polyether amine having a number-average molecular weight of about 450 to about 200,000 Daltons, and (iii) at least one oligomer of the formula:

R1-(PS)-R2 to form a hydrogel; wherein:
(A) PS is a linear polymeric segment comprising ethylene oxide monomers or a combination of ethylene oxide and propylene oxide monomers, wherein said ethylene oxide monomers comprise at least about 50 weight percent of said polymeric segment;
(B) R1 is at least one nucleophilic group capable of reacting with aldehyde groups to form at least one reversible covalent bond;
(C) R2 is at least one functional group which is not capable of reacting with an aldehyde, a primary amine, a secondary amine, or R1 to form a covalent bond, such that said oligomer does not induce gelation when mixed in an aqueous medium with either (i) alone or (ii) alone;
(D) said oligomer has a weight-average molecular weight of about 200 to about 10,000 Daltons; and
(E) said oligomer is water soluble; and
b) treating said hydrogel to remove at least a portion of said solvent to form the dried hydrogel.

In another embodiment, the invention provides a composition comprising the reaction product of:
a) at least one oxidized polysaccharide containing aldehyde groups, having a weight-average molecular weight of about 1,000 to about 1,000,000 Daltons, said oxidized polysaccharide having an equivalent weight per aldehyde group of about 65 to about 1500 Daltons;
b) at least one water-dispersible, multi-arm polyether amine wherein at least three of the arms are terminated by at least one primary amine group, said multi-arm polyether amine having a number-average molecular weight of about 450 to about 200,000 Daltons; and
c) at least one oligomer of the formula:

R1-(PS)-R2 wherein:
(i) PS is a linear polymeric segment comprising ethylene oxide monomers or a combination of ethylene oxide and propylene oxide monomers, wherein said ethylene oxide monomers comprise at least about 50 weight percent of said polymeric segment;
(ii) R1 is at least one nucleophilic group capable of reacting with aldehyde groups to form at least one reversible covalent bond;
(iii) R2 is at least one functional group which is not capable of reacting with an aldehyde, a primary amine, a secondary amine, or R1 to form a covalent bond, such that said oligomer does not induce gelation when mixed in an aqueous medium with either (a) alone or (b) alone;
(iv) said oligomer has a weight-average molecular weight of about 200 to about 10,000 Daltons; and
(v) said oligomer is water soluble.

In another embodiment, the invention provides a method for applying a coating to an anatomical site on tissue of a living organism comprising:
applying to the site
a) at least one oxidized polysaccharide containing aldehyde groups, having a weight-average molecular weight of about 1,000 to about 1,000,000 Daltons, said oxidized polysaccharide having an equivalent weight per aldehyde group of about 65 to about 1500 Daltons;
b) at least one water-dispersible, multi-arm polyether amine wherein at least three of the arms are terminated by at least one primary amine group, said multi-arm polyether amine having a number-average molecular weight of about 450 to about 200,000 Daltons; and
c) at least one oligomer of the formula:

R1-(PS)-R2 wherein:
(i) PS is a linear polymeric segment comprising ethylene oxide monomers or a combination of ethylene oxide and propylene oxide monomers, wherein said ethylene oxide monomers comprise at least about 50 weight percent of said polymeric segment;
(ii) R1 is at least one nucleophilic group capable of reacting with aldehyde groups to form at least one reversible covalent bond;
(iii) R2 is at least one functional group which is not capable of reacting with an aldehyde, a primary amine, a secondary amine, or R1 to form a covalent bond, such that said oligomer does not induce gelation when mixed in an aqueous medium with either (a) alone or (b) alone;
(iv) said oligomer has a weight-average molecular weight of about 200 to about 10,000 Daltons; and
(v) said oligomer is water soluble;
wherein (a), (b), and (c) are applied to the site in any order, or (a), (b), and (c) are premixed and the resulting mixture is applied to the site before the mixture completely cures.

In another embodiment, the invention provides a method for decreasing the degradation time of a hydrogel formed from at least one oxidized polysaccharide (component A) and at least one water-dispersible, multi-arm polyether amine (component B), said at least one oxidized polysaccharide containing aldehyde groups, having a weight-average molecular weight of about 1,000 to about 1,000,000 Daltons and an equivalent weight per aldehyde group of about 65 to about 1500 Daltons, and said at least one water-dispersible, multi-arm polyether amine wherein at least three of its arms terminated by at least one primary amine group, said multi-arm polyether amine having a number-average molecular weight of about 450 to about 200,000 Daltons; said method comprising the step of: contacting component A and component B in the presence of an aqueous medium and at least one oligomer of the formula:

R1-(PS)-R2 wherein:
i) PS is a linear polymeric segment comprising ethylene oxide monomers or a combination of ethylene oxide and propylene oxide monomers, wherein said ethylene oxide monomers comprise at least about 50 weight percent of said polymeric segment;
(ii) R1 is at least one nucleophilic group capable of reacting with aldehyde groups to form at least one reversible covalent bond;
(iii) R2 is at least one functional group which is not capable of reacting with an aldehyde, a primary amine, a secondary amine, or R1 to form a covalent bond, such that said oligomer does not induce gelation when mixed in an aqueous medium with either component A alone or component B alone;
(iv) said oligomer has a weight-average molecular weight of about 200 to about 10,000 Daltons; and (v) said oligomer is water soluble;
wherein, in said method the oligomer is used in an amount sufficient to decrease the degradation time of the resulting hydrogel under predetermined conditions by at least about 10% compared to that of the hydrogel formed under said predetermined conditions, but in the absence of said oligomer.

DETAILED DESCRIPTION

As used above and throughout the description of the invention, the following terms, unless otherwise indicated, shall be defined as follows:

The term "oxidized polysaccharide" refers to a polysaccharide which has been reacted with an oxidizing agent to introduce aldehyde groups into the molecule.

The term "equivalent weight per aldehyde group" refers to the molecular weight of the oxidized polysaccharide divided by the number of aldehyde groups introduced in the molecule.

The term "water-dispersible, multi-arm polyether amine" refers to a polyether having three or more polymer chains ("arms"), which may be linear or branched, emanating from a central structure, which may be a single atom, a core molecule, or a polymer backbone, wherein at least three of the branches ("arms") are terminated by at least one primary amine group. The water-dispersible, multi-arm polyether amine is water soluble or is able to be dispersed in water to form a colloidal suspension capable of reacting with a second reactant in aqueous solution or dispersion.

The term "dispersion" as used herein, refers to a colloidal suspension capable of reacting with a second reactant in an aqueous medium.

The term "polyether" refers to a polymer having the repeat unit [—O—R]—, wherein R is a hydrocarbylene group having 2 to 5 carbon atoms. The polyether may also be a random or block copolymer comprising different repeat units having different R groups.

The term "hydrocarbylene group" refers to a divalent group formed by removing two hydrogen atoms, one from each of two different carbon atoms, from a hydrocarbon.

The term "branched polyether" refers to a polyether having one or more branch points ("arms"), including star, dendritic, comb, and hyperbranched polyethers.

The term "dendritic polyether" refers to a highly branched polyether having a tree-like structure.

The term "comb polyether" refers to a polyether having a main chain with multiple trifunctional branch points from each of which a linear arm emanates.

The term "star polyether" refers to a polyether having a central branch point, which may be a single atom or a chemical group, from which linear arms emanate.

The term "hyperbranched polyether" refers to a highly branched polyether having fewer branches and less regular branching than a dendritic polyether.

The term "primary amine" refers to a neutral amino group having two free hydrogens. The amino group may be bound to a primary, secondary or tertiary carbon.

The term "multi-functional amine" refers to a chemical compound comprising at least two functional groups, at least one of which is a primary amine group.

The term "crosslink" refers to a bond or chain of atoms attached between and linking two different polymer chains.

The term "crosslink density" is herein defined as the reciprocal of the average number of chain atoms between crosslink connection sites.

The term "% by weight", also referred to herein as "wt %" refers to the weight percent relative to the total weight of the solution or dispersion, unless otherwise specified.

The term "nucleophilic group" as used herein refers to an atom or a group of atoms within a molecule that form a chemical bond by donating electrons, i.e., a nucleophilic group is an electron donating group.

The term "functional group" as used herein refers to an atom or a group of atoms within a molecule that undergo characteristic chemical reactions.

The term "reversible covalent bond" as used herein refers to a covalent bond that undergoes a reversible reaction.

The term "reversible reaction" as used herein refers to a chemical reaction that can be made to proceed in either direction (i.e., forward or reverse) by changing physical conditions.

The term "covalent bond" as used herein refers to a type of chemical bonding that is characterized by the sharing of pairs of electrons between atoms.

The term "water soluble" as used herein means that a material is capable of being dissolved in water at a concentration of at least 1 weight percent and remains in solution at a temperature of 18 to 25° C. and atmospheric pressure (i.e., 740 to 760 mm of mercury).

The term "anatomical site" refers to any external or internal part of the body of humans or animals.

The term "tissue" refers to any biological tissue, both living and dead, in humans or animals.

The term "hydrogel" refers to a water-swellable polymeric matrix, consisting of a three-dimensional network of macromolecules held together by covalent crosslinks, that can absorb a substantial amount of water to form an elastic gel.

The term "dried hydrogel" refers to a hydrogel that has been treated to remove at least a portion of the solvent contained therein. Preferably, substantially all of the solvent is removed from the hydrogel.

The term "PEG" as used herein refers to polyethylene glycol.

The term "$M_w$" as used herein refers to the weight-average molecular weight.

The term "$M_n$" as used herein refers to the number-average molecular weight.

The term "medical application" refers to medical applications as related to humans and animals.

The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "wt %" means percent by weight, "mol %" means mole percent, "Vol" means volume, "v/v" means volume per volume, "Da" means Dalton(s), "kDa" means kiloDalton(s), the designation "10K" means that a polymer molecule possesses a number-average molecular weight of 10 kiloDaltons, "M" means molarity, "Pa" means pascal(s), "kPa" means kilopascal(s), "mTorr" means milliTorr", "$^1$H NMR" means proton nuclear magnetic resonance spectroscopy, "ppm" means parts per million, "PBS" means phosphate-buffered saline, "RT" means room temperature, "rpm" means revolutions per minute, "psi" means pounds per square inch.

A reference to "Aldrich" or a reference to "Sigma" means the said chemical or ingredient was obtained from Sigma-Aldrich, St. Louis, Mo.

Disclosed herein is a hydrogel tissue adhesive formed by reacting an oxidized polysaccharide with a water-dispersible, multi-arm polyether amine wherein the hydrogel comprises an oligomer additive which decreases the degradation time of the hydrogel. The hydrogel may be useful as a tissue adhesive or sealant for medical applications that require more rapid degradation, including but not limited to, use as a hemostat sealant, or to prevent undesired tissue-to-tissue adhesions resulting from trauma or surgery.

Oxidized Polysaccharides

Oxidized polysaccharides useful in the invention include, but are not limited to, oxidized derivatives of: dextran, carboxymethyldextran, starch, agar, cellulose, hydroxyethylcellulose, carboxymethylcellulose, pullulan, inulin, levan, and hyaluronic acid. The starting polysaccharides are available commercially from sources such as Sigma Chemical Co. (St. Louis, Mo.). Typically, polysaccharides are a heterogeneous mixture having a distribution of different molecular weights, and are characterized by an average molecular weight, for example, the weight-average molecular weight ($M_w$), or the number average molecular weight ($M_n$), as is known in the art. Suitable oxidized polysaccharides have a weight-average molecular weight of about 1,000 to about 1,000,000 Daltons, more particularly about 3,000 to about 250,000 Daltons, more particularly about 5,000 to about 100,000 Daltons, and more particularly about 10,000 to about 60,000 Daltons. In one embodiment, the oxidized polysaccharide is oxidized dextran, also referred to herein as dextran aldehyde.

Oxidized polysaccharides may be prepared by oxidizing a polysaccharide to introduce aldehyde groups using any suitable oxidizing agent, including but not limited to, periodates, hypochlorites, ozone, peroxides, hydroperoxides, persulfates, and percarbonates. For example, the polysaccharide may be oxidized by reaction with sodium periodate as described by Mo et al. (*J. Biomater. Sci. Polymer Edn.* 11:341-351, 2000). The polysaccharide may be reacted with different amounts of periodate to give polysaccharides with different degrees of oxidation and therefore, different amounts of aldehyde groups. Additionally, the oxidized polysaccharide may be prepared using the method described by Cohen et al. (copending and commonly owned International Patent Application Publication No. WO 2008/133847). That method of making an oxidized polysaccharide comprises a combination of precipitation and separation steps to purify the oxidized polysaccharide formed by oxidation of the polysaccharide with periodate, as described in detail in the Examples herein below, and provides an oxidized polysaccharide with very low levels of iodine-containing species. The degree of oxidation, also referred to herein as the oxidation conversion, of the oxidized polysaccharide may be determined using methods known in the art. For example, the degree of oxidation of the oxidized polysaccharide may be determined using the method described by Hofreiter et al. (*Anal Chem.* 27:1930-1931, 1955). In that method, the amount of alkali consumed per mole of dialdehyde in the oxidized polysaccharide, under specific reaction conditions, is determined by a pH titration. Alternatively, the degree of oxidation of the oxidized polysaccharide may be determined using nuclear magnetic resonance (NMR) spectroscopy, as described in detail in the Examples herein below. In one embodiment, the equivalent weight per aldehyde group of the oxidized polysaccharide is from about 65 to about 1500 Daltons, more particularly from about 90 to about 1500 Daltons.

Water-Dispersible, Multi-Arm Polyether Amines

As defined herein, a water-dispersible, multi-arm polyether amine is a water-dispersible polyether having the repeat unit [—O—R]—, wherein R is a hydrocarbylene group having 2 to 5 carbon atoms. Typically, multi-arm polyether amines suitable for use herein have a number-average molecular weight from about 450 to about 200,000 Daltons, more particularly, from about 2,000 to about 40,000 Daltons, and more particularly about 2,000 to about 10,000 Daltons. Suitable water-dispersible, multi-arm polyether amines include, but are not limited to, amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines, sold under the trade name Jeffamine® triamines, by Huntsman LLC. (Houston, Tex.). Examples of star polyethylene oxide amines, include, but are not limited to, various multi-arm polyethylene glycol amines, and star polyethylene glycols having 3, 4, 6, or 8 arms terminated with primary amines (referred to herein as 3, 4, 6, or 8-arm star PEG amines, respectively). Examples of suitable Jeffaminetriamines include, but are not limited to, Jeffamine® T-403 (CAS No. 39423-51-3), Jeffamine® T-3000 (CAS No. 64852-22-8), and Jeffamine® T-5000 (CAS No. 64852-22-8). In one embodiment, the water-dispersible multi-arm polyether amine is an eight-arm polyethylene glycol having eight arms terminated by a primary amine group and having a number-average molecular weight of about 10,000 Daltons.

The multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4, 6, and 8-arm star polyethylene glycols, available from companies such as Nektar Transforming Therapeutics; SunBio, Inc., Anyang City, South Korea; NOF Corp., Tokyo, Japan; or JenKem Technology USA, Allen, Tex.) using the method described by Buckmann et al. (*Makromol. Chem.* 182:1379-1384, 1981). In that method, the multi-arm polyethylene glycol is reacted with thionyl bromide to convert the hydroxyl groups to bromines, which are then converted to amines by reaction with ammonia at 100° C. The method is broadly applicable to the preparation of other multi-arm polyether amines. Additionally, multi-arm polyether amines may be prepared from multi-arm polyols using the method described by Chenault (copending and commonly owned U.S. Patent Application Publication No. 2007/0249870). In that method, the multi-arm polyether is reacted with thionyl chloride to convert the hydroxyl groups to chlorine groups, which are then converted to amines by reaction with aqueous or anhydrous ammonia. Other methods that may be used for preparing multi-arm polyether amines are described by Merrill et al. in U.S. Pat. No. 5,830,986, and by Chang et al. in WO 97/30103.

Water-dispersible, multi-arm polyether amines suitable for use herein may also be multi-arm branched end polyether amines, as described by Arthur (copending and commonly owned International Patent Application Publication No. WO 2008/066787). The multi-arm branched end polyether amines are branched polymers having two or three primary amine groups at the end of each of the polymer arms. The multiplicity of functional groups increases the statistical probability of reaction at a given chain end and allows more efficient incorporation of the branched molecules into a polymer network. The starting materials used to prepare the branched end polyether amines may be multi-arm polyether polyols including, but not limited to, comb and star polyether polyols. The multi-arm branched end polyether amines can be prepared by attaching multiple amine groups to the ends of the multi-arm polyether polyols by reaction with the hydroxyl groups using methods well known in the art. For example, a branched end polyether amine having two amine functional groups on each end of the polymer arms can be to prepared by reacting the starting material, as listed above, with thionyl chloride in a suitable solvent such as toluene to give the chloride derivative, which is subsequently reacted with tris (2-aminoethyl)amine to give the multi-arm branched end polyether amine having two primary amine groups at the end of the polymer arms.

It should be recognized that the water-dispersible, multi-arm polyether amines are generally a somewhat heterogeneous mixture having a distribution of arm lengths and in some cases, a distribution of species with different numbers of arms. When a multi-arm polyether amine has a distribution of species having different numbers of arms, it can be referred to based on the average number of arms in the distribution. For example, in one embodiment the multi-arm polyether amine is an 8-arm star PEG amine, which comprises a mixture of multi-arm star PEG amines, some having less than and some having more than 8 arms; however, the multi-arm star PEG amines in the mixture have an average of 8 arms. Therefore, the terms "8-arm", "6-arm", "4-arm" and "3-arm" as used herein to refer to multi-arm polyether amines, should be construed as referring to a heterogeneous mixture having a distribution of arm lengths and in some cases, a distribution of species with different numbers of arms, in which case the number of arms recited refers to the average number of arms in the mixture.

Oligomer Additives

The oligomer additive serves to decrease the degradation time of the hydrogel resulting from the reaction of the oxidized polysaccharide and the water-dispersible, multi-arm polyether amine, and may or may not decrease the rate of gelation to form the hydrogel, depending on the concentration used. Suitable oligomer additives have the general formula:

R1-(PS)-R2 (1)

wherein: PS is a linear polymeric segment comprising ethylene oxide monomers or a combination of ethylene oxide and propylene oxide monomers, wherein the ethylene oxide monomers comprise at least about 50 wt % of the polymeric segment, more particularly at least about 60 wt %, more particularly at least about 70 wt %, more particularly at least about 80 wt %, more particularly at least about 90 wt %, and more particularly 100 wt % of the polymeric segment. PS may comprise random or block copolymers of ethylene oxide and propylene oxide. The polymeric segment may also comprise a linker to attach R1 and R2 to the ends of the polymeric segment, as described below. In one embodiment, PS is a linear polymeric segment terminating with a methylene group at both ends of the segment; the segment is derived from a polymer selected from the group consisting of: polyethylene oxide, block or random copolymers of polyethylene oxide and polypropylene oxide, and triblock copolymers of polyethylene oxide and polypropylene oxide. As used herein "derived from a polymer" when referring to a polymeric segment, means that the polymeric segment has the structure of the polymer without the polymer's terminal end groups (e.g., hydroxyl groups), and therefore both ends of the polymeric segment are terminated with a methylene group.

R1 is at least one nucleophilic group capable of reacting with aldehyde groups to form at least one reversible covalent bond. Suitable R1 groups include, but are not limited to, primary amine, secondary amine, and carboxyhydrazide. R2 is at least one functional group which is not capable of reacting with an aldehyde, a primary amine, a secondary amine, or R1 to form a covalent bond such that said oligomer does not induce gelation when mixed in an aqueous medium with either the oxidized polysaccharide alone or the water-dispersible, multi-arm polyether amine alone (i.e., the oligomer does not function as a crosslinking agent). Suitable R2 groups include, but are not limited to, hydroxy, methoxy, ethoxy, propoxy, butoxy, and phenoxy. Suitable oligomers have a weight-average molecular weight of about 200 to about 10,000 Daltons, more particularly about 350 to about 5,000 Daltons, and more particularly about 350 to about 2,000 Daltons. The oligomer is water soluble.

Suitable oligomers are available commercially from companies such as Sigma-Aldrich (St. Louis, Mo.), or can be synthesized using methods known in the art. For example, a methoxy PEG amine may be prepared by mesylation of a suitable molecular weight methoxy PEG alcohol (available from Sigma-Aldrich), followed by amination of the mesylated intermediate, as described in detail in the Examples herein below. Additionally, various linking groups at the ends of the polymeric segment may be used to attach R1 and R2 to the polymeric segment. Nonlimiting examples of linking groups include S—R$_2$—CH$_2$, and NH—R$_2$—CH$_2$, wherein R$_2$ is an alkylene group having from 1 to 5 carbon atoms. For example, a suitable molecular weight methoxy PEG alcohol may be reacted with methanesulfonyl chloride in a suitable solvent, such as dichloromethane, in the presence of a base such as tripentylamine, to form the mesylate derivative, which is subsequently reacted with a diamine such as ethylene diamine to form an oligomer wherein R1 (a primary amine group) is attached through the linker NH—CH$_2$—CH$_2$, which is at one end of the polymeric segment (i.e., NH—CH$_2$—CH$_2$—R1).

In one embodiment, the oligomer is methoxy polyethylene glycol amine wherein PS is a linear polymeric segment derived from polyethylene oxide, R1 is a primary amine group and R2 is a methoxy group.

In one embodiment, the oxidized polysaccharide containing aldehyde groups is oxidized dextran, the water-dispersible, multi-arm polyether amine is a multi-arm polyethylene glycol amine, and the oligomer is methoxy polyethylene glycol amine wherein PS is a linear polymeric segment derived from polyethylene oxide, R1 is a primary amine and R2 is methoxy.

Methods of Using the Hydrogel Tissue Adhesive

The hydrogel tissue adhesive disclosed herein may be used in various forms. In one embodiment, the oxidized polysaccharide containing aldehyde groups, the water-dispersible, multi-arm polyether amine, and the oligomer additive are used as components of aqueous solutions or dispersions. To prepare an aqueous solution or dispersion comprising an oxidized polysaccharide (referred to herein as the "first aqueous solution or dispersion"), at least one oxidized polysaccharide is added to water to give a concentration of about 5% to about 40% by weight, more particularly from about 5% to about 30% by weight, and more particularly from about 10% to about 30% by weight relative to the total weight of the solution or dispersion. Additionally, a mixture of at least two different oxidized polysaccharides having different weight-average molecular weights, different degrees of oxidation, or both different weight-average molecular weights and different degrees of oxidation may be used. Where a mixture of oxidized polysaccharides is used, the total concentration of the oxidized polysaccharides is about 5% to about 40% by weight, more particularly from about 5% to about 30% by weight, and more particularly from about 10% to about 30% by weight relative to the total weight of the solution or dispersion.

Similarly, to prepare an aqueous solution or dispersion comprising a water-dispersible, multi-arm polyether amine (referred to herein as the "second aqueous solution or dispersion"), at least one water-dispersible, multi-arm polyether amine is added to water to give a concentration of about 5% to about 70% by weight, more particularly from about 20% to about 50% by weight relative to the total weight of the solution or dispersion. The optimal concentration to be used depends on the intended application and on the concentration of the oxidized polysaccharide used in the first aqueous solution or dispersion. Additionally, a mixture of different water-dispersible, multi-arm polyether amines having different number-average molecular weights, different numbers of arms, or both different number-average molecular weights and different numbers of arms may be used. Where a mixture of water-dispersible, multi-arm polyether amines is used, the total concentration of the multi-arm polyether amines is about 5% to about 70% by weight, more particularly from about 20% to about 50% by weight relative to the total weight of the solution or dispersion.

An effective amount of at least one oligomer additive, as described above, is added to at least one of the following solutions or dispersions: the aqueous solution or dispersion comprising the oxidized polysaccharide (i.e., the first aqueous solution or dispersion), the aqueous solution or dispersion comprising the water-dispersible, multi-arm polyether amine (i.e., the second aqueous solution or dispersion), or a third aqueous solution or dispersion. The oligomer additive has the greatest effect on the degradation time of the hydrogel when it is added to the aqueous solution or dispersion comprising the oxidized polysaccharide (i.e., the first aqueous solution or dispersion), as shown in the Examples herein below. Additionally, the oligomer enhances the dissolution rate of the oxidized polysaccharide when added during the preparation of the first aqueous solution or dispersion, as shown in the Examples herein below.

The solutions or dispersions containing the oligomer additive may be prepared in any number of ways. For example, the oligomer may be added to the first aqueous solution or dispersion containing the oxidized polysaccharide, prepared as described above, or the second aqueous solution or dispersion containing the water-dispersible, multi-arm polyether amine, prepared as described above. Alternatively, the oligomer may first be dissolved in water and the oxidized polysaccharide or multi-arm polyether amine may be subsequently added. Additionally an aqueous solution or dispersion containing the oligomer may be combined with either the first or second aqueous solutions or dispersions. An effective amount of the oligomer is any amount sufficient to provide the desired degradation time for the hydrogel. In general, the larger the amount of the oligomer used, the greater is the effect on reducing the degradation time of the hydrogel. At low loadings of the oligomer, i.e., where the aldehyde-reactive group (R1) represents about 5 mole percent or less relative to the total number of moles of aldehyde on the oxidized polysaccharide, the oligomer reduces the degradation time without affecting the gelation time to form the hydrogel or other hydrogel properties. At higher loadings of the oligomer (i.e., where the aldehyde-reactive group (R1) represents greater than 5 mole percent relative to the total number of moles of aldehyde on the oxidized polysaccharide), the oligomer retards gelation as well as reduces the degradation time. The amount of the oligomer to be used to achieve the desired degradation time can be determined by one skilled in the art using routine experimentation.

In one embodiment, an effective amount of the oligomer additive is about 0.25% to about 30% by weight, more particularly about 0.5% to about 30% by weight, and more particularly about 0.75% to about 20% by weight relative to the total weight of the aqueous solution or dispersion, specifically, the first aqueous solution or dispersion, the second aqueous solution or dispersion, or the third aqueous solution or dispersion.

In one embodiment, the amount of oligomer used is sufficient to provide a decrease in degradation time, under predetermined conditions, of at least about 10% compared to that of the hydrogel formed under the same conditions, but in the absence of the oligomer. For any set of predetermined conditions, the degradation time of the resulting hydrogel can be determined using methods known in the art. For example, after the hydrogel is formed, it can be incubated in an aqueous medium with shaking at a specified temperature and agitation speed and the time required for the hydrogel to dissolve can be measured, as described in the Examples herein below.

For use on living tissue, it is preferred that the first aqueous solution or dispersion and the second aqueous solution or dispersion be sterilized to prevent infection. Any suitable sterilization method known in the art that does not adversely affect the ability of the components to react to form an effective hydrogel may be used, including, but not limited to, electron beam irradiation, gamma irradiation, ethylene oxide sterilization, or ultra-filtration through a 0.2 μm pore membrane. If the oligomer is contained in a third aqueous solution or dispersion, that solution or dispersion can also be sterilized using the methods listed above.

The first aqueous solution or dispersion, the second aqueous solution or dispersion, and/or the third aqueous solution or dispersion (if used) may further comprise various additives depending on the intended application. Preferably, the additive does not interfere with effective gelation to form a hydrogel. The amount of the additive used depends on the particular application and may be readily determined by one skilled in the art using routine experimentation. For example, the first aqueous solution or dispersion, the second aqueous solution or dispersion, and/or the third aqueous solution or dispersion may comprise at least one additive selected from pH modifiers, antimicrobials, colorants, surfactants, pharmaceutical drugs and therapeutic agents.

The first aqueous solution or dispersion, the second aqueous solution or dispersion, and/or the third aqueous solution or dispersion may optionally include at least one pH modifier to adjust the pH of the solution(s) or dispersion(s). Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The first aqueous solution or dispersion, the second aqueous solution or dispersion, and/or the third aqueous solution or dispersion may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The first aqueous solution or dispersion, the second aqueous solution or dispersion, and/or the third aqueous solution or dispersion may optionally include at least one colorant to enhance the visibility of the solution(s) or dispersion(s). Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, and carmine.

The first aqueous solution or dispersion, the second aqueous solution or dispersion, and/or the third aqueous solution or dispersion may optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the first aqueous solution or dispersion, the second aqueous solution or dispersion, and/or the third aqueous solution or dispersion may optionally include at least one pharmaceutical drug or therapeutic agent. Suitable drugs and therapeutic agents are well known in the art (for example see the United States Pharmacopeia (USP), Physician's Desk Reference (Thomson Publishing), The Merck Manual of Diagnosis and Therapy 18th ed., Mark H. Beers and Robert Berkow (eds.), Merck Publishing Group, 2006; or, in the case of animals, The Merck Veterinary Manual, 9 th ed., Kahn, C. A. (ed.), Merck Publishing Group, 2005). Nonlimiting examples include, but are not limited to, anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; fibrinolytic agents such as a tissue plasminogen activator and streptokinase; anti-coagulants such as heparin, hirudin, ancrod, dicumarol, sincumar, iloprost, L-arginine, dipyramidole and other platelet function inhibitors; antibodies; nucleic acids; peptides; hormones; growth factors; cytokines; chemokines; clotting factors; endogenous clotting inhibitors; antibacterial agents; antiviral agents; antifungal agents; anti-cancer agents; cell adhesion inhibitors; healing promoters; vaccines; thrombogenic agents, such as thrombin, fibrinogen, homocysteine, and estramustine; radio-opaque compounds, such as barium sulfate and gold particles and radiolabels.

Additionally, the second aqueous solution or dispersion comprising the water-dispersible, multi-arm polyether amine may optionally comprise at least one other multi-functional amine having one or more primary amine groups to provide other beneficial properties, such as hydrophobicity or modified crosslink density. The multi-functional amine is capable of inducing gelation when mixed with an oxidized polysaccharide in an aqueous solution or dispersion. The multi-functional amine may be a second water-dispersible, multi-arm polyether amine, such as those described above, or another type of multi-functional amine, including, but not limited to, linear and branched diamines, such as diaminoalkanes, polyaminoalkanes, and spermine; branched polyamines, such as polyethylenimine; cyclic diamines, such as N, N'-bis (3-aminopropyl)piperazine, 5-amino-1,3,3-trimethylcyclohexanemethylamine, 1,3-bis(aminomethyl)cyclohexane, 1,4-diaminocyclohexane, and p-xylylenediamine; aminoalkyltrialkoxysilanes, such as 3-aminopropyltrimethoxysilane and 3-aminopropyltriethoxysilane; aminoalkyldialkoxyalkylsilanes, such as 3-aminopropyldiethoxymethylsilane, dihydrazides, such as adipic dihydrazide; linear polymeric diamines, such as linear polyethylenimine, α,ω-amino-terminated polyethers, α,ω-bis(3-aminopropyl)polybutanediol, β,ω-1-amino-terminated polyethers (linear Jeffamines®); comb polyamines, such as chitosan, polyallylamine, and polylysine, and di- and polyhydrazides, such as bis(carboxyhydrazido)polyethers and poly(carboxyhydrazido) star polyethers. Many of these compounds are commercially available from companies such as Sigma-Aldrich and Huntsman LLC. Typically, if present, the multi-functional amine is used at a concentration of about 5% by weight to about 1000% by weight relative to the weight of the multi-arm polyether amine in the aqueous solution or dispersion.

In one embodiment, the first aqueous solution or dispersion and the second aqueous solution or dispersion, at least one of which comprises the oligomer additive, may be used to apply a coating to an anatomical site on tissue of a living organism. The two aqueous solutions or dispersions may be applied to the site in any number of ways. Once both solutions or dispersions are combined on a site, they crosslink to form a hydrogel, a process referred to herein as curing, typically in about 2 to 3 minutes. The hydrogel provides a coating on the site.

In one embodiment, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In another embodiment, the two aqueous solutions or dispersions are mixed manually before application to the site. The resulting mixture is then applied to the site before it completely cures using a suitable applicator, as described above.

In another embodiment, the first aqueous solution or dispersion and the second aqueous solution or dispersion are applied to the site simultaneously where they mix to form a hydrogel. For example, the two aqueous solutions or dispersions may be contained in separate barrels of a double-barrel syringe. In this way the two aqueous solutions or dispersions are applied simultaneously to the site with the syringe. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47). The two aqueous solutions or dispersions may also be applied to the site using a dual-lumen catheter, such as those available from Bistech, Inc. (Woburn, Mass.). Additionally, injection devices for introducing two liquid components endoscopically into the body simultaneously are known in the art and may be adapted for the delivery of the two aqueous solutions or dispersions disclosed herein (see for example, Linder et al., U.S. Pat. No. 5,322, 510).

In another embodiment, the first aqueous solution or dispersion and the second aqueous solution or dispersion may be premixed and delivered to the site using a double barrel syringe containing a motionless mixer, such as that available from ConProtec, Inc. (Salem, N.H.) or Mixpac Systems AG (Rotkreuz, Switzerland). Alternatively, the mixing tip may be equipped with a spray head, such as that described by Cruise et al. in U.S. Pat. No. 6,458,147. Additionally, the mixture of the two aqueous solutions or dispersions from the double-barrel syringe may be applied to the site using a catheter or endoscope. Devices for mixing a two liquid component tissue adhesive and delivering the resulting mixture endoscopically are known in the art and may be adapted for the mixing and delivery of the two aqueous solutions or dispersions disclosed herein (see for example, Nielson, U.S. Pat. No. 6,723,067; and Redl et al., U.S. Pat. No. 4,631,055).

In another embodiment, the two aqueous solutions or dispersions may be applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862).

In another embodiment, the two aqueous solutions or dispersions may be applied to the site using a minimally invasive surgical applicator, such as those described by Sawhney (U.S. Pat. No. 7,347,850).

In another embodiment wherein the oligomer additive is contained in a third aqueous solution or dispersion, the three aqueous solutions or dispersions may be applied to the anatomical site in any order using any of the methods described above. In this embodiment, the delivery device used may be modified to deliver the three aqueous solutions or dispersions. For example, the double-barrel syringe may be modified to have three barrels, one for each of the aqueous solutions or dispersions.

In another embodiment, the hydrogel tissue adhesive of the invention may be used to bond at least two anatomical sites together. In this embodiment, the first aqueous solution or dispersion is applied to at least one anatomical site, and the second aqueous solution or dispersion is applied to at least one of either the same site or one other site using the methods described above. The two or more sites are contacted and held together manually or using some other means, such as a surgical clamp, for a time sufficient for the mixture to cure. Alternatively, a mixture of the two aqueous solutions or dispersions is applied to at least one of the anatomical sites to be bonded using methods described above. The two or more sites are contacted and held together manually or using some other means, such as a surgical clamp, for a time sufficient for the mixture to cure.

In another embodiment wherein the oligomer is contained in a third aqueous solution or dispersion and used along with the first aqueous solution or dispersion and the second aqueous solution or dispersion to bond at least two anatomical sites together, each of the three aqueous solutions or dispersions may be applied to at least one anatomical site in any order. The aqueous solutions or dispersions may be applied to the same site or to different sites. Alternatively, the three aqueous solutions or dispersions may be premixed using any of the methods described above, and the resulting mixture applied to at least one of the anatomical sites to be bonded before the mixture completely cures. The two or more sites are then contacted and held together manually or using some other means, such as a surgical clamp, for a time sufficient for the mixture to cure.

In another embodiment, the oxidized polysaccharide, the water-dispersible, multi-arm polyether amine, and the oligomer may be used in the form of finely divided powders. The powders may be prepared using any suitable method. For example, the aqueous solutions or dispersions described above may be dried using heat, vacuum, a combination of heat and vacuum, or by lyophilization, to form powders. Optionally, the powders may be comminuted into finer particles using methods known in the art including, but not limited to, grinding, milling, or crushing with a mortar and pestle. The finely divided powders may be sterilized using the methods described above. The finely divided powders may be applied to an anatomical site on tissue of a living organism in a variety of ways. For example, the powders may be individually applied to the site in any order by sprinkling or spraying. Additionally, the powders may be premixed and the resulting mixture applied to the site by sprinkling or spraying. The powders may be hydrated on the site by the addition of an aqueous solution such as water or a suitable buffer (e.g., phosphate-buffered saline) or by the physiological fluids present at the site. The finely divided powders may also be used to bond two anatomical sites together as described above for the aqueous solutions or dispersions. Alternatively, the powders may be hydrated with water or a suitable aqueous solution prior to use to form the first and second aqueous solutions or dispersions, described above.

In another embodiment, the hydrogel tissue adhesive disclosed herein may be used in the form of a dried hydrogel. In this embodiment, a dried hydrogel is prepared by combining in a solvent at least one oxidized polysaccharide with at least one water-dispersible, multi-arm polyether amine and at least one oligomer of formula (1) to form a hydrogel, and treating the hydrogel to remove at least a portion of the solvent to form the dried hydrogel. Suitable solvents include, but are not limited to, water, ethanol, isopropanol, tetrahydrofuran, hexanes, polyethylene glycol, and mixtures thereof. If two different solvents are used the two solvents are miscible with each other. In one embodiment, the solvent is water. The oxidized polysaccharide, the water-dispersible, multi-arm polyether amine, and the oligomer may be combined in various ways. For example, the first aqueous solution or dispersion comprising the oxidized polysaccharide and the second aqueous solution or dispersion comprising the water-dispersible, multi-arm polyether amine, at least one of which comprises the oligomer additive, may be prepared and mixed as described above to form the hydrogel. Alternatively, the first aqueous solution or dispersion comprising the oxidized polysaccharide, the second aqueous solution or dispersion comprising the water-dispersible, multi-arm polyether amine, and a third aqueous solution or dispersion comprising the oligomer additive may be prepared and mixed as described above to form the hydrogel. The solutions or dispersions used to prepare the hydrogel may further comprise various additives depending on the intended application. Any of the additives described above may be used. The hydrogel is then treated to remove at least a portion of the solvent contained therein to form the dried hydrogel. Preferably, substantially all of the solvent is removed from the hydrogel. The solvent may be removed from the hydrogel using methods known in the art, for example, using heat, vacuum, a combination of heat and vacuum, or flowing a stream of dry air or a dry inert gas such as nitrogen over the hydrogel. The dried hydrogel may be sterilized using the methods described above. The dried hydrogel may be applied to an anatomical site in a number of ways, as described below. The dried hydrogel may be hydrated on the site by the addition of a suitable aqueous solution such as water or a buffer (e.g., phosphate-buffered saline) or by the physiological fluids present at the site.

In one embodiment, the dried hydrogel may be used in the form of a film. The dried hydrogel film may be formed by casting a mixture of the solutions or dispersions on a suitable substrate and treating the resulting hydrogel to form a dried hydrogel film. The dried hydrogel film may be applied directly to an anatomical site. Additionally, the dried hydrogel film may be used to bond two anatomical sites together.

In another embodiment, the dried hydrogel may be used in the form of finely divided particles. The dried hydrogel particles may be formed by comminuting the dried hydrogel using methods known in the art, including, but not limited to, grinding, milling, or crushing with a mortar and pestle. The dried hydrogel may be applied to an anatomical site in a variety of ways, such as sprinkling or spraying, and may also be used to bond two anatomical sites together.

Method for Decreasing Degradation Time

In another embodiment, the invention provides a method for decreasing the degradation time of a hydrogel formed from at least one oxidized polysaccharide (component A) and at least one water-dispersible, multi-arm polyether amine (component B), said at least one oxidized polysaccharide containing aldehyde groups, having a weight-average molecular weight of about 1,000 to about 1,000,000 Daltons and an equivalent weight per aldehyde group of about 65 to about 1500 Daltons, and said at least one water-dispersible, multi-arm polyether amine having at least three of its arms terminated by at least one primary amine group, and a number-average molecular weight of about 450 to about 200,000 Daltons; said method comprising the step of:

contacting component A and component B in the presence of an aqueous medium and at least one oligomer of formula (1) having a weight-average molecular weight of about 200 to about 10,000 Daltons, to form a mixture that forms a resulting hydrogel, wherein, in said method, the oligomer is used in an amount sufficient to decrease the degradation time of the resulting hydrogel under predetermined conditions by at least about 10% compared to that of the hydrogel formed under said conditions, but in the absence of said oligomer.

For any set of predetermined conditions, the degradation time of the resulting hydrogel can be determined using methods known in the art. For example, after the hydrogel is formed, it can be incubated in an aqueous medium with shaking at a specified temperature and agitation speed and the time required for the hydrogel to dissolve can be measured, as described in the Examples herein below. The addition of the oligomer under the same predetermined conditions results in decreasing the degradation time by at least about 10%.

Kits

In one embodiment, the invention provides a kit comprising at least one oxidized polysaccharide containing aldehyde groups, at least one water-dispersible, multi-arm polyether amine wherein at least three of the arms are terminated by at least one primary amine group, and at least one oligomer of formula (1), as described above.

In another embodiment, the kit comprises a first aqueous solution or dispersion comprising at least one oxidized polysaccharide containing aldehyde groups; a second aqueous solution or dispersion comprising at least one water-dispersible, multi-arm polyether amine; and at least one oligomer of formula (1). The oligomer is a component of at least one of the first aqueous solution or dispersion, the second aqueous solution or dispersion, or a third aqueous solution or dispersion, as described above. Each of the aqueous solutions or dispersions may be contained in any suitable vessel, such as a vial or a syringe barrel.

In another embodiment, the kit comprises at least one oxidized polysaccharide, at least one water-dispersible, multi-arm polyether amine, and at least one oligomer of formula (1) in the form of finely divided powders, as described above. The powders may be contained in separate containers or they may be premixed and contained in a single container. The kit may also comprise an aqueous solution for hydrating the powders.

In another embodiment, the kit comprises a dried hydrogel as described above. The dried hydrogel may be in the form of a film, finely divided particles, or other dried forms. The kit may further comprise an aqueous solution for hydrating the dried hydrogel. The dried hydrogel particles may be contained in any suitable container.

Medical Applications:

The hydrogel disclosed herein may be useful as a tissue adhesive or sealant for medical applications, including but not limited to, use as a hemostat sealant or to prevent undesired tissue-to-tissue adhesions resulting from trauma or surgery. In these applications, the oxidized polysaccharide, the water-dispersible multi-arm polyether amine, and the oligomer additive or the dried hydrogel may be applied to the desired anatomical site using the methods described above.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Reagents

Methoxy PEG amines (CAS No. 80506-64-5) of several average molecular weights (i.e., 5000, 2000, and 750 Da) were obtained from Sigma-Aldrich. A methoxy PEG amine having an average molecular weight of 350 Da was synthesized as described below. A methoxy PEG amine having an average molecular weight of 750 Da was also synthesized using the same procedure. The methoxy PEG amine having an average molecular weight of 750 Da that was obtained from Sigma-Aldrich was used in the following Examples, except where use of the synthesized material is specifically indicated. In the following Examples, methoxy PEG amines are referred to as "MPA" followed by the average molecular weight. For example, MPA 2000 is a methoxy PEG amine having an average molecular weight 2000 Da.

Preparation of MPA 350

A 350 molecular weight methoxy PEG amine was synthesized using a two-step procedure involving mesylation of a similar molecular weight methoxy PEG alcohol, followed by amination of the mesylated intermediate.

Step 1—Mesylation of Methoxy PEG Alcohol:

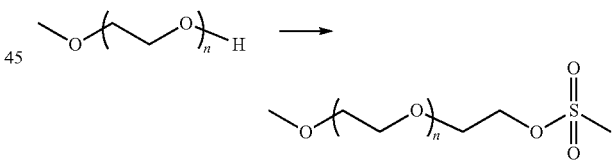

In the first step, 17.502 g (0.05 mol) of methoxy PEG alcohol having an average molecular weight of 350 Da (Sigma-Aldrich) was dissolved in 250 mL of methylene chloride at room temperature (RT) in a 500 mL, 3-neck, round-bottom flask. To this solution was added 13.94 mL (0.1 mol) of triethylamine, followed by the dropwise addition of 7.74 mL (0.1 mol) of methanesulfonyl chloride (fuming, slight exotherm). The resulting reaction solution was stirred overnight at RT while maintaining a nitrogen blanket. Then, the reaction solution was diluted with 250 mL of chloroform and washed with 1.0 M potassium hydrogen phosphate (2×100 mL), 1.0 M potassium carbonate (2×100 mL), and deionized water (3×100 mL). The organic layer was dried over magnesium sulfate, filtered, and concentrated using a rotary evaporator to produce an amber oil product. The amber oil product was dried under high vacuum overnight (i.e., less than 100 mTorr (13.3 Pa)). The final weight of the dried product was 20.32 g. The identity of the product was confirmed by $^1$H NMR in deuterated chloroform.

Step 2—Amination of Mesylation Product:

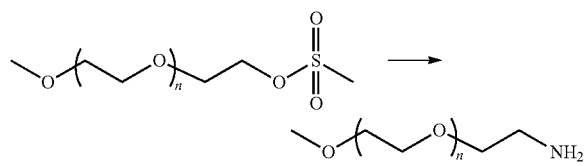

In the second step, 19.8 g of the mesylated product from step 1 was dissolved in 400 mL of ammonium hydroxide solution (28-30% in water) in a tightly capped bottle and stirred at RT for 5 days. The solution was then sparged with nitrogen for 6 hours to drive off residual ammonia (to approximately 85% of the original volume). The resulting solution was diluted with 200 mL of 2.0 M potassium carbonate solution and extracted with chloroform (3×150 mL). The chloroform layers were combined, dried over magnesium sulfate, and concentrated using a rotary evaporator to produce a pale yellow oil. The oil was dried further under high vacuum (i.e., less than 90 mTorr (12.0 Pa)). The final weight of the resulting product was 14.4 g. The identity of the product was confirmed by $^1$H NMR in deuterated dimethyl sulfoxide.

Preparation of MPA 750

A 750 molecular weight methoxy PEG amine was synthesized using the two-step procedure described above for the preparation of MPA 350. The starting methoxy PEG alcohol having an average molecular weight of about 750 Daltons was obtained from Sigma-Aldrich.

Preparation of Dextran Aldehyde (D10-50)

Dextran aldehyde is made by oxidizing dextran in aqueous solution with sodium metaperiodate. An oxidized dextran with about 50% oxidation conversion (i.e., about half of the glucose rings in the dextran polymer are oxidized to dialdehydes) is prepared from dextran having a weight-average molecular weight of 8,500 to 11,500 Daltons (Sigma) by the method described by Cohen et al. (copending and commonly owned International Patent Application Publication No. WO 2008/133847). A typical procedure is described here.

A 20-L reactor equipped with a mechanical stirrer, addition funnel, internal temperature probe, and nitrogen purge is charged with 1000 g of the dextran and 9.00 L of de-ionized water. The mixture is stirred at ambient temperature to dissolve the dextran and then cooled to 10 to 15° C. To the cooled dextran solution is added over a period of an hour, while keeping the reaction temperature below 25° C., a solution of 1000 g of sodium periodate dissolved in 9.00 L of de-ionized water. Once all the sodium periodate solution has been added, the mixture is stirred at 20 to 25° C. for 4 more hours. The reaction mixture is then cooled to 0° C. and filtered to clarify. Calcium chloride (500 g) is added to the filtrate, and the mixture is stirred at ambient temperature for 30 min and then filtered. Potassium iodide (400 g) is added to the filtrate, and the mixture is stirred at ambient temperature for 30 min. A 3-L portion of the resulting red solution is added to 9.0 L of acetone over a period of 10 to 15 min with vigorous stirring by a mechanical stirrer during the addition. After a few more minutes of stirring, the agglomerated product is separated from the supernatant liquid. The remaining red solution obtained by addition of potassium iodide to the second filtrate is treated in the same manner as above. The combined agglomerated product is broken up into pieces, combined with 2 L of methanol in a large stainless steel blender, and blended until the solid becomes granular. The granular solid is recovered by filtration and dried under vacuum with a nitrogen purge. The granular solid is then hammer milled to a fine powder. A 20-L reactor is charged with 10.8 L of de-ionized water and 7.2 L of methanol, and the mixture is cooled to 0° C. The granular solid formed by the previous step is added to the reactor and the slurry is stirred vigorously for one hour. Stirring is discontinued, and the solid is allowed to settle to the bottom of the reactor. The supernatant liquid is decanted by vacuum, 15 L of methanol is added to the reactor, and the slurry is stirred for 30 to 45 min while cooling to 0° C. The slurry is filtered in portions, and the recovered solids are washed with is methanol, combined, and dried under vacuum with a nitrogen purge to give about 600 g of the oxidized dextran, which is referred to herein as D10-50.

The degree of oxidation of the product is determined by proton NMR to be about 50% (equivalent weight per aldehyde group=146). In the NMR method, the integrals for two ranges of peaks are determined, specifically, —O$_2$CHx- at about 6.2 parts per million (ppm) to about 4.15 ppm (minus the HOD peak) and —OCHx- at about 4.15 ppm to about 2.8 ppm (minus any methanol peak if present). The calculation of oxidation level is based on the calculated ratio (R) for these areas, specifically, R=(OCH)/(O$_2$CH).

Preparation of Eight-Arm PEG 10K Octaamine (P8-10-1):

Eight-arm PEG 10K octaamine ($M_n$=10 kDa) is synthesized using the two-step procedure described by Chenault in co-pending and commonly owned U.S. Patent Application Publication No. 2007/0249870. In the first step, the 8-arm PEG 10K chloride is made by reaction of thionyl chloride with the 8-arm PEG 10K octaalcohol. In the second step, the 8-arm PEG 10K chloride is reacted with aqueous ammonia to yield the 8-arm PEG 10K octaamine. A typical procedure is described here.

The 8-arm PEG 10K octaalcohol ($M_n$=10000; SunBright HGEO-10000; NOF Corp.), (100 g in a 500-mL round-bottom flask) is dried either by heating with stirring at 85° C. under vacuum (0.06 mm of mercury (8.0 Pa)) for 4 hours or by azeotropic distillation with 50 g of toluene under reduced pressure (2 kPa) with a pot temperature of 60° C. The 8-arm PEG 10K octaalcohol is allowed to cool to room temperature and thionyl chloride (35 mL, 0.48 mol) is added to the flask, which is equipped with a reflux condenser, and the mixture is heated at 85° C. with stirring under a blanket of nitrogen for 24 hours. Excess thionyl chloride is removed by rotary evaporation (bath temp 40° C.). Two successive 50-mL portions of toluene are added and evaporated under reduced pressure (2 kPa, bath temperature 60° C.) to complete the removal of thionyl chloride. Proton NMR results from one synthesis are:

$^1$H NMR (500 MHz, DMSO-d6) δ 3.71-3.69 (m, 16H), 3.67-3.65 (m, 16H), 3.50 (s, ~800H).

The 8-arm PEG 10K octachloride (100 g) is dissolved in 640 mL of concentrated aqueous ammonia (28 wt %) and heated in a pressure vessel at 60° C. for 48 hours. The solution is sparged for 1-2 hours with dry nitrogen to drive off 50 to 70 g of ammonia. The solution is then passed through a column (500 mL bed volume) of strongly basic anion exchange resin (Purolite® A-860, The Purolite Co., Bala-Cynwyd, Pa.) in the hydroxide form. The eluant is collected and three 250-mL portions of de-ionized water are passed through the column and also collected. The aqueous solutions are combined, concentrated under reduced pressure (2 kPa, bath temperature 60° C.) to about 200 g, frozen in portions and lyophilized to give the 8-arm PEG 10K octaamine, referred to herein as P8-10-1, as a colorless waxy solid.

General Methods
Preparation of Hydrogel Precursor Solutions

Oxidized dextran solutions and multi-arm PEG amine solutions were prepared by dissolving the desired amount of oxidized dextran or multi-arm PEG amine in distilled water to achieve the desired concentration (weight %). The multi-arm PEG amine typically dissolved readily at room temperature. In the absence of additives, the oxidized dextran dissolved slowly at room temperature, but dissolved completely after heating at 37° C. overnight.

Various methoxy PEG amines were added to either the oxidized dextran or multi-arm PEG amine solutions, or both. A formulation with an additive was designed by removing a quantity of water from a control formulation and replacing it with the same quantity of the additive. Specific procedures for introducing additives are described in the Examples below.

Gelation Time Measurements

The gelation time upon mixing the hydrogel precursor solutions was studied to assess the ease of application for in vivo use. The oxidized dextran solution (0.10 mL) was placed in a vial. Then, 0.10 mL of the multi-arm PEG amine solution was added to the vial and the mixture was immediately stirred with a small spatula until the mixture gelled to the point where it held its shape without flowing. This time was measured and taken as the gelation time.

Degradation Time Measurements

The degradation behavior of hydrogels at 37° C. in Dulbecco's phosphate buffered saline at pH 7.4 (DPBS, 1× without calcium or magnesium, Invitrogen, Carlsbad, Calif.; cat. 14190 or Mediatech, Herndon, Va.; cat. 21-031) was studied as follows to assess acceptability of the hydrogel formulation for in vivo use. A double-barrel syringe (1:1 v/v) with a 16-step static mixing tip was used to prepare a hydrogel test strip. The oxidized dextran solution was added to one side of the double-barrel syringe, and the multi-arm PEG amine solution was added to the other side. The mixing tip was cut 5 mm from the end to make a larger exit diameter.

A hydrogel formulation was cast using the double-barrel syringe with mixing tip into a 1 mm thick by 6.8 mm wide by approximately 70 mm long mold. After 15 min, the ends were trimmed and the resulting hydrogel strip was cut into 2 test strips, each 30 mm×6.8 mm×1 mm in size. After weighing, the strips were each placed in a 20 mL vial containing DPBS buffer. The vials were capped and placed in an incubator shaker at 37° C. and 80 rpm. The hydrogel test strips were typically weighed at 2 hours and 5 hours on the first day, and every 24 hours thereafter until the weight of the test strip was less than 50% of its initial weight. At each time, the hydrogel strip was removed from buffer, drained of excess liquid, and weighed. The strip was then placed in a vial with fresh DPBS and returned to the incubator.

This procedure resulted in a plot of hydrogel weight versus time, expressed as percent of initial weight versus time. Typically, there was an initial increase in weight due to equilibrium swelling, followed by some additional swelling as crosslinks are broken and finally a loss of weight as soluble degradation products diffuse from the hydrogel. Fragments of the hydrogel may linger for some time. The time to 50% of the initial weight was used as a meaningful parameter of the degradation curve for comparing formulations. This time, referred to herein as the degradation time, was estimated by interpolation between the time point at which the weight is just above 50% and the time point at which the weight is just below 50%. Reported values are averages of determinations on the two hydrogel strip samples.

Examples 1-4

Effect of Methoxy PEG Amines of Different Molecular Weight on Dissolution of Oxidized Dextran The purpose of these Examples was to demonstrate the effect of methoxy PEG amines on the dissolution rate of oxidized dextran.

Methoxy PEG amines having average molecular weights of 750, 2000, and 5000 Da (obtained from Sigma-Aldrich) were each dissolved in deionized water in a vial. Then, oxidized dextran D10-50 powder was poured into the vial all at once. The vial was capped and then stirred with a magnetic stirrer at RT. For comparison, the same amount of D10-50 was poured into a vial with deionized water without the methoxy PEG amine (Example 4, Comparative). The compositions and observations are summarized in Table 1.

TABLE 1

Effect of Methoxy PEG amine on Dissolution Rate of Oxidized Dextran

| Example | MPA Molecular Weight (Da) | MPA (wt %) | D10-50 (wt %) | Dissolution Time |
|---|---|---|---|---|
| 1 | 750 | 8% | 8% | ≤5 min |
| 2 | 2000 | 8% | 8% | 5-10 min |
| 3 | 5000 | 8% | 8% | >24 hours |
| 4 Comparative | none | 0% | 8% | >24 hours |

The results in Table 1 suggest that in compositions containing 8 wt % MPA 750 (Example 1) and MPA 2000 (Example 2) the oxidized dextran dissolved completely at room temperature in just a few minutes. In a composition containing MPA 5000 (Example 3) and the comparative formulation without MPA (Example 4, Comparative), the oxidized dextran did not dissolve fully even after 24 hours. Those compositions required a few hours in an incubator at 37° C. to effect complete dissolution of the oxidized dextran.

Examples 5-8

Gelation Times for the Formation of Hydrogels from Oxidized Dextran and a Multi-Arm PEG Amine in the Presence of Methoxy PEG Amines The purpose of these Examples was to demonstrate the formation of hydrogels from an oxidized dextran (D10-50) and a multi-arm PEG amine (P8-10-1) in the presence of a methoxy PEG amine additive. The time required to form the hydrogel (i.e., the gelation time) was also determined.

Hydrogels were formed by mixing an aqueous solution containing an oxidized dextran (i.e., D10-50) containing a methoxy PEG amine with an aqueous solution containing a multi-arm PEG amine (i.e., P8-10-1) using the method described above in General Methods. The oxidized dextran solutions used are described in Examples 1-4. The results are summarized in Table 2.

TABLE 2

Gelation Times for the Formation of Hydrogels

| Example | Oxidized Dextran Solution | P8-10-1 (wt %) | Gelation Time (sec) |
|---|---|---|---|
| 5 | Example 1 | 30% | 90-120 |
| 6 | Example 2 | 30% | 25-30 |
| 7 | Example 3 | 30% | 8-12 |
| 8 Comparative | Example 4 Comparative | 30% | 8-12 |

The results given in Table 2 suggest that the lower molecular weight MPA additives that dramatically enhance dissolution of dextran-aldehyde (Examples 5 and 6) also significantly retard gelation time compared to the comparative Example without the methoxy PEG amine additive (Example 8, Comparative).

Examples 9-12

Effect of Different Concentrations of Methoxy PEG Amine 750 on the Dissolution of Oxidized Dextran Various concentrations of MPA 750 were each dissolved in deionized water in a vial. Then oxidized dextran D10-50 powder was poured into the vial all at once. The vial was capped and then stirred with a magnetic stirrer at room temperature until the D10-50 was dissolved. The compositions and observations are summarized in Table 3.

TABLE 3

Effect of MPA 750 on Dissolution Rate of Oxidized Dextran

| Example | MPA 750 (wt %) | D10-50 (wt %) | Dissolution Time (min) |
|---|---|---|---|
| 9 | 8% | 8% | 1-2 |
| 10 | 4% | 8% | 1-2 |
| 11 | 2% | 8% | 2-3 |
| 12 | 1% | 8% | 5 (slight remaining particulate) |

The results shown in Table 3 suggest that only 1 or 2 wt % of MPA 750 (Examples 11 and 12) enhances the dissolution rate of D10-50 (see Example 4, Comparative).

Examples 13-16

Gelation Times for the Formation of Hydrogels from Oxidized Dextran and a Multi-Arm PEG Amine in the Presence of MPA 750

The purpose of these Examples was to demonstrate the formation of hydrogels from an oxidized dextran (D10-50) and a multi-arm PEG amine (P8-10-1) in the presence of MPA 750 at different concentrations. The time required to form the hydrogel (i.e., the gelation time) was also determined.

Hydrogels were formed by mixing an aqueous solution containing an is oxidized dextran (i.e., D10-50) containing MPA 750 with an aqueous solution containing a multi-arm PEG amine (i.e., P8-10-1) using the method described above in General Methods. The oxidized dextran solutions used are described in Examples 9-12. The results are summarized in Table 4.

TABLE 4

Gelation Times for the Formation of Hydrogels

| Example | Oxidized Dextran Solution | P8-10-1 (wt %) | Gelation Time (sec) |
|---|---|---|---|
| 13 | Example 9 | 30% | 48-58 |
| 14 | Example 10 | 30% | 22-27 |
| 15 | Example 11 | 30% | 13-18 |
| 16 | Example 12 | 30% | 10-14 |

The data in Table 4 suggest that at the lower MPA 750 concentrations, i.e., 2 wt % (Example 15) and 1 wt % (Example 16), the effect on gelation time is fairly minor (see Example 8, Comparative). At 2 wt % MPA 750 and 8 wt % D10-50, complete reaction of the amines on MPA 750 only represents about 5% of the available aldehydes on D10-50. Therefore, 95% of the aldehyde groups of D10-50 would still be available to crosslink when combined with the P8-10-1 multi-arm PEG amine.

Examples 17-21

Effect of Different Concentrations of Methoxy PEG Amine 750 on the Dissolution of High Concentrations of Oxidized Dextran Various concentrations of MPA 750 were each dissolved in deionized water in a vial. Then oxidized dextran D10-50 powder was poured into the vial all at once. The vial was capped and then stirred with a magnetic stirrer at room temperature until the D10-50 was dissolved. The compositions and observations are summarized in Table 5.

TABLE 5

Effect of MPA 750 on Dissolution Rate of Oxidized Dextran

| Example | MPA 750 (wt %) | D10-50 (wt %) | Dissolution Time, Partial | Dissolution Time, Complete (hours) |
|---|---|---|---|---|
| 17 | 20% | 25% | 5 min (some dissolved) | >72 |
| 18 | 10% | 25% | 10 min (some dissolved) | 72 |
| 19 | 5% | 25% | 10 min (most dissolved) | 2.5 |
| 20 | 2.5% | 25% | 5 min (most dissolved) | 4 |
| 21 Comparative | 0% | 25% | 4.5 hours (gelatinous) | 72 |

The results shown in Table 5 suggest that, although the addition of MPA 750 does not result in complete dissolution of 25 wt % D10-50 in minutes, its effect is still dramatic. In the absence of MPA 750 (Example 21, Comparative), the mixture of D10-50 and water is an unstirrable solid for several hours until it slowly becomes gelatinous. By contrast, the addition of MPA 750 enables the mixture to quickly become flowable and for part or most of the D10-50 to dissolve in minutes.

Examples 22-26

Gelation Times for the Formation of Hydrogels from Oxidized Dextran at High Concentration and a Multi-Arm PEG Amine in the Presence of Different Concentrations MPA 750

The purpose of these Examples was to demonstrate the formation of hydrogels from an oxidized dextran (D10-50) at high concentration and a multi-arm PEG amine (P8-10-1) in the presence of MPA 750 at different concentrations. The time required to form the hydrogel (i.e., the gelation time) was also determined.

Hydrogels were formed by mixing an aqueous solution containing a high concentration of oxidized dextran (i.e., D10-50) containing MPA 750 with an aqueous solution containing a multi-arm PEG amine (i.e., P8-10-1) using the method described above in General Methods. The oxidized dextran solutions used are described in Examples 17-21. The results are summarized in Table 6.

TABLE 6

Gelation Times for the Formation of Hydrogels

| Example | Oxidized Dextran Solution | P8-10-1 (wt %) | Gelation Time (sec) |
|---|---|---|---|
| 22 | Example 17 | 30% | 40-50 |
| 23 | Example 18 | 30% | 15-20 |
| 24 | Example 19 | 30% | 6-12 |
| 25 | Example 20 | 30% | 5-10 |
| 26 Comparative | Example 21 Comparative | 30% | 5-8 |

The data in Table 6 suggest that at the lower MPA 750 concentrations, i.e., 5 wt % (Example 24) and 2.5 wt % (Example 25), the effect on gelation time is fairly minor as the gelation times are comparable to the gelation time in the absence of MPA 750 (Example 26, Comparative).

Examples 27-32

Effect of Methoxy PEG Amines Having Different Molecular Weight on In Vitro Degradation Time of Hydrogels The effect of methoxy PEG amine addition was studied using a base formulation of 12% D10-50 oxidized dextran in aqueous solution and 40% P8-10-1 multi-arm PEG amine in aqueous solution. Formulations were prepared incorporating various amounts of methoxy PEG amine of 750, 2000, or 5000 average molecular weight in place of water in the oxidized dextran solution. The degradation time of the resulting hydrogels was determined as described in General Methods. The formulations and degradation times are shown in Table 7.

TABLE 7

In Vitro Degradation Time Of Hydrogels

| Example | D10-50 (wt %) | P8-10-1 (wt %) | MPA MW (Da) | MPA (wt %) | Degradation Time (hours) |
|---|---|---|---|---|---|
| 27 Comparative | 12% | 40% | none | 0% | 151 |
| 28 | 12% | 40% | 750 | 1% | 88 |
| 29 | 12% | 40% | 2000 | 2% | 113 |
| 30 | 12% | 40% | 2000 | 4% | 36 |
| 31 | 12% | 40% | 5000 | 5% | 47 |
| 32 | 12% | 40% | 5000 | 10% | 26 |

The results shown in Table 7 suggest that the addition of methoxy PEG amine promotes degradation of the hydrogels compared with the same formulation without methoxy PEG amine (Example 27, Comparative). Although the addition of all of the methoxy PEG amines reduced degradation time, the lower molecular weight methoxy PEG amines had a greater effect at lower concentrations. For example, only 1% of MPA 750 reduced the degradation time from 151 to 88 hours (compare Example 27 with Example 28), while 2% of MPA 2000 reduced the degradation time from 151 to 113 hours (compare Example 27 with Example 29).

Examples 33-39

Effect of Methoxy PEG Amines on Gelation Time and In Vitro Degradation Time

The effect of methoxy PEG amine addition on gelation time and in vitro degradation time was studied using base formulations of 8 wt % and 10 wt % D10-50 oxidized dextran in aqueous solution and 30 wt % P8-10-1 multi-arm PEG amine in aqueous solution. Formulations were prepared incorporating various amounts of methoxy PEG amine of 350 or 750 molecular weight in place of water in the oxidized dextran solution. The gelation times and in vitro degradation times were determined as described in General Methods. The formulations and results are shown in Table 8.

TABLE 8

Gelation Times and In Vitro Degradation Times of Hydrogels

| Example | D10-50 (wt %) | P8-10-1 (wt %) | MPA MW (Da) | MPA (wt %) | Gelation Time (sec) | Degradation Time (hours) |
|---|---|---|---|---|---|---|
| 33 Comparative | 8% | 30% | none | 0% | 7-10 | 26 |
| 34 | 8% | 30% | 350 | 1% | 8-16 | 4 |
| 35 | 8% | 30% | 750 | 2% | 9-15 | 4 |
| 36 Comparative | 10% | 30% | none | 0% | 4-8 | 85 |
| 37 | 10% | 30% | 350 | 1.5% | 7-14 | 4 |
| 38 | 10% | 30% | 750 | 2% | 7-12 | 18 |
| 39 | 10% | 30% | 750 | 3% | 7-14 | 4 |

The results shown in Table 8 suggest that at these low levels of methoxy PEG amine additive, the effect on gelation time is minor. However, the shortening of degradation time is dramatic. For example, addition of only 1 wt % MPA 350 or 2 wt % MPA 750 reduces degradation time from 26 hours to 4 hours for the base formulation with 8 wt % D10-50 (Examples 34 and 35 compared to Example 33, Comparative). Similar large effects are seen when MPA 350 or 750 is added to the base formulation with 10 wt % D10-50 (Examples 37, 38, and 39 compared to Example 36, Comparative).

Example 40

Effect of Methoxy PEG Amine Added to Multi-Arm PEG Amine Solution on Gelation Time and In Vitro Degradation Time To compare the effect of adding methoxy PEG amine to the multi-arm PEG amine solution with the effect of adding it to the oxidized dextran solution, the formulation of Example 39 was repeated, except that the 3% MPA 750 was added to the multi-arm PEG amine solution, replacing an equal amount of water. The gelation time and in vitro degradation time were determined using the same methods used for Examples 33 through 39. The gelation time of this formulation was 4-8 sec and the degradation time was 40 hours.

Comparison of these results with those for Example 36, Comparative and Example 39 illustrates the significant influence of the manner of addition of the MPA. The degradation time was reduced from 85 to 40 hours when 3 wt % MPA 750 was added to the P8-10-1 solution (Example 36, Comparative versus Example 40). But the reduction was from 85 to 4 hours when the same amount of MPA 750 was instead added to the D10-50 solution (Example 36, Comparative versus Example 39). Gelation time was not measurably affected by the addition of 3 wt % MPA 750 to the P8-10-1 solution, unlike the modest effect on gelation time observed when 3 wt % MPA 750 was added to the D10-50 solution. Therefore, these results demonstrate that adding the methoxy PEG amine to the oxidized dextran solution has a larger effect on degradation time than adding it to the multi-arm PEG amine solution.

Examples 41 and 42

Cytotoxicity Testing of Methoxy PEG Amines

The purpose of these Examples was to demonstrate the safety of methoxy PEG amines in an in vitro cytotoxicity test.

Methoxy PEG amine solutions (1.0 wt %) were prepared and tested for cytotoxicity. MPA 750 (102.2 mg) from Sigma-Aldrich (Example 41) and MPA 750 (103.3 mg) synthesized as described in Reagents (Example 42) were placed in Falcon™ test tubes. Ten milliliters of Dulbecco's modified essential medium (DMEM) was added to each tube to give a 10 mg/mL working solution concentration. After the MPA dissolved in the cell culture medium, both media turned bright purple, indicating that MPA is responsible for an increase in pH. Both MPA solutions were transferred to a cell culture flask and incubated at 37° C. under 5% $CO_2$ in an incubator for at least one hour to allow the pH of the media to equilibrate to neutral pH. Both MPA solutions were filtered through a 0.22 μm filter unit before applying to the cells.

NIH 3T3 P20 cells were detached from the walls of a flask with the aid of trypsin and re-suspended at a suitable cell concentration of about a half million cells per well of a six well plate for samples, positive and negative control. To the positive control well was added 100 μl of Tween® 20 mixed with the cells. The negative control well cells were cultured with DMEM culture medium. The cells were imaged using a light microscope after 20 hours and 48 hours for extended toxicity evaluation. Both samples showed no toxicity for cells. Cell growth was the same as for the negative control. Therefore, 1% MPA 2, whether from Sigma-Aldrich (Example 41) or synthesized in the lab (Example 42), showed no toxicity to NIH 3T3 P20 cells, which suggests that the methoxy PEG amines are safe as an additive to hydrogels for use in the body.

Examples 43-45

Cytotoxicity Testing of Hydrogels Containing Methoxy PEG Amines

The purpose of these Examples was to demonstrate the safety of hydrogels containing methoxy PEG amines in an in vitro cytotoxicity test.

Hydrogels were prepared by dispensing precursor solutions, as shown in Table 9, from a double-barrel syringe through a 16-step mixing tip into a 0.45 mm thickness mold. The resulting gelled samples were cut into round disks with a weight range of 30-35 mg. The disks were placed into the wells of a six-well plate. All tools employed in the hydrogel formation were cleaned with 70% ethanol prior to use to minimize contamination.

TABLE 9

Precursor Solutions for Preparation of Hydrogels

| Example | D10-50 (wt %) | P8-10-1 (wt %) | MPA 750 (wt %) |
|---|---|---|---|
| 43, Comparative | 12% | 40% | none |
| 44 | 12% | 40% | 1% (from Sigma-Aldrich) |
| 45 | 12% | 40% | 1% (synthesized) |

NIH 3T3 P20 cells were detached from the walls of a flask with the aid of trypsin and re-suspended at a suitable cell concentration of about half million cells per well of a six well plate for samples, positive and negative control. To the positive control well was added 100 μl of Tween® 20 mixed with cells. The negative control well cells were cultured with DMEM culture medium. The cells were imaged using a light microscope after 20 hours and 48 hours for extended toxicity evaluation. All three samples showed no toxicity for cells. Cell growth was the same as for the negative control. For Examples 44 and 45, cells grew nicely even near the hydrogels, even better than for Example 43, Comparative without MPA 750. Therefore, hydrogels with MPA 750, whether from Sigma-Aldrich (Example 44) or synthesized in the lab (Example 45), showed no toxicity to NIH 3T3 P20 cells, which suggests that the hydrogels containing methoxy PEG amines are safe for use in the body.

Examples 46-51

Burst Strength Testing of Hydrogel Formulations Containing Methoxy PEG Amine

The purpose of these Examples was to demonstrate the burst strength of a seal made with hydrogels containing a methoxy PEG amine additive of an incision made in swine uterine horn.

A 5 to 6-mm incision was made using a #15 surgical blade in a 6 to 8-cm section of clean, fresh swine uterine horn. The wound was sealed by applying a hydrogel formulation using a double-barrel syringe with a mixing tip at a thickness of 1-2 mm. After the hydrogel had been allowed to cure (typically 2-3 min), one end of the section of uterine horn was secured to a metal nipple with a nylon cable tie, and the other end was clamped shut. The metal nipple was connected by plastic tubing to a syringe pump equipped with a pressure meter. The section of uterine horn was submerged in a beaker of water, and purple dyed water was pumped by the syringe pump into the section at 11 mL/min. The pressure at which the sealed wound leaked was noted and recorded as the burst strength. Reported values are typically averages of 3 to 4 measurements. The burst strengths of several hydrogel formulations containing MPA 750 were determined. The formulations and results, given as the mean and standard deviation, are summarized in Table 10.

TABLE 10

Burst Strength of Hydrogels Containing Methoxy PEG Amine

| Example | D10-50 (wt %) | P8-10-1 (wt %) | MPA 750 (wt %) | Burst Strength (psi) |
|---|---|---|---|---|
| 46 Comparative | 12% | 30% | none | 2.46 ± 0.04 (17.0 ± 0.3 kPa) |
| 47 | 12% | 30% | 0.75% | 1.33 ± 0.35 (9.17 ± 2 kPa) |

TABLE 10-continued

Burst Strength of Hydrogels Containing Methoxy PEG Amine

| Example | D10-50 (wt %) | P8-10-1 (wt %) | MPA 750 (wt %) | Burst Strength (psi) |
|---|---|---|---|---|
| 48 | 12% | 30% | 1.5% | 1.63 ± 0.2 (11.2 ± 1 kPa) |
| 49 Comparative | 12% | 40% | none | 2.95 ± 1.17 (20.3 ± 8.1 kPa) |
| 50 | 12% | 40% | 0.75% | 2.49 ± 0.6 (17.2 ± 4 kPa) |
| 51 | 12% | 40% | 1.5% | 3.09 ± 0.31 (21.3 ± 2 kPa) |

The results shown in Table 10 suggest that formulations containing MPA 750 at levels that enhance dissolution of oxidized dextran and promote degradation also exhibit burst strength that is adequate for adhesive and other in vivo applications.

What is claimed is:

1. A kit for forming a hydrogel comprising:
   a) at least one oxidized polysaccharide containing aldehyde groups, said oxidized polysaccharide having a weight-average molecular weight of about 1,000 to about 1,000,000 Daltons and having an equivalent weight per aldehyde group of about 65 to about 1500 Daltons;
   b) at least one water-dispersible, multi-arm polyether amine wherein at least three of the arms are terminated by at least one primary amine group, said multi-arm polyether amine having a number-average molecular weight of about 450 to about 200,000 Daltons; and
   c) at least one oligomer of the formula:

R1-(PS)-R2 wherein:
   (i) PS is a linear polymeric segment comprising ethylene oxide monomers or a combination of ethylene oxide and propylene oxide monomers, wherein said ethylene oxide monomers comprise at least 50 weight percent of said polymeric segment;
   (ii) R1 is at least one nucleophilic group capable of reacting with aldehyde groups to form at least one reversible covalent bond;
   (iii) R2 is at least one functional group which is not capable of reacting with an aldehyde, a primary amine, a secondary amine, or R1 to form a covalent bond, such that said oligomer does not induce gelation when mixed in an aqueous medium with either (a) alone or (b) alone;
   (iv) said oligomer has a weight-average molecular weight of about 200 to about 10,000 Daltons; and
   (v) said oligomer is water soluble; and
   wherein said hydrogel has a decreased degradation time compared to a hydrogel formed under the same conditions in the absence of said oligomer.

2. The kit according to claim 1 wherein the oxidized polysaccharide is a component of a first aqueous solution or dispersion, the water-dispersible, multi-arm polyether amine is a component of a second aqueous solution or dispersion, and the oligomer is a component of at least one of: (i) the first aqueous solution or dispersion; (ii) the second aqueous solution or dispersion; or (iii) a third aqueous solution or dispersion.

3. The kit according to claim 2 wherein the first aqueous solution or dispersion comprises the oxidized polysaccharide at a concentration of about 5% to about 40% by weight relative to the total weight of the solution or dispersion.

4. The kit according to claim 2 wherein the second aqueous solution or dispersion comprises the water-dispersible, multi-arm polyether amine at a concentration of about 5% to about 70% by weight relative to the total weight of the solution or dispersion.

5. The kit according to claim 2 wherein at least one of the first aqueous solution or dispersion, the second aqueous solution or dispersion, or the third aqueous solution or dispersion comprises the oligomer at a concentration of about 0.25% to about 30% by weight relative to the total weight of the solution or dispersion.

6. The kit according to claim 1 wherein the oxidized polysaccharide is selected from the group consisting of oxidized derivatives of: dextran, carboxymethyldextran, starch, agar, cellulose, hydroxyethylcellulose, carboxymethylcellulose, pullulan, inulin, levan, and hyaluronic acid.

7. The kit according to claim 6 wherein the oxidized polysaccharide is oxidized dextran.

8. The kit according to claim 1 wherein the water-dispersible, multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

9. The kit according to claim 1 wherein PS is a linear polymeric segment terminating with a methylene group at both ends of said segment, wherein said segment is derived from a polymer selected from the group consisting of: polyethylene oxide, block or random copolymers of polyethylene oxide and polypropylene oxide, and triblock copolymers of polyethylene oxide and polypropylene oxide.

10. The kit according to claim 1 wherein R1 is selected from the group consisting of primary amine, secondary amine, and carboxyhydrazide.

11. The kit according to claim 1 wherein R2 is selected from the group consisting of hydroxy, methoxy, ethoxy, propoxy, butoxy, and phenoxy.

12. The kit according to claim 1 wherein the oligomer is methoxy polyethylene glycol amine wherein PS is a linear polymeric segment derived from polyethylene oxide, R1 is a primary amine, and R2 is methoxy.

13. A dried hydrogel formed by a process comprising the steps of:
   a) combining in a solvent (i) at least one oxidized polysaccharide containing aldehyde groups, said oxidized polysaccharide having a weight-average molecular weight of about 1,000 to about 1,000,000 Daltons and having an equivalent weight per aldehyde group of about 65 to about 1500 Daltons with (ii) at least one water-dispersible, multi-arm polyether amine, wherein at least three of the arms are terminated by at least one primary amine group, said multi-arm polyether amine having a number-average molecular weight of about 450 to about 200,000 Daltons, and (iii) at least one oligomer of the formula:

R1-(PS)-R2 to form a hydrogel; wherein:

(A) PS is a linear polymeric segment comprising ethylene oxide monomers or a combination of ethylene oxide and propylene oxide monomers, wherein said ethylene oxide monomers comprise at least 50 weight percent of said polymeric segment;

(B) R1 is at least one nucleophilic group capable of reacting with aldehyde groups to form at least one reversible covalent bond;

(C) R2 is at least one functional group which is not capable of reacting with an aldehyde, a primary amine, a secondary amine, or R1 to form a covalent bond, such that said oligomer does not induce gelation when mixed in an aqueous medium with either (i) alone or (ii) alone;

(D) said oligomer has a weight-average molecular weight of about 200 to about 10,000 Daltons; and (E) said oligomer is water soluble; and b) treating said hydrogel to remove at least a portion of said solvent to form the dried hydrogel;

wherein said dried hydrogel has a decreased degradation time compared to a dried hydrogel formed under the same conditions in the absence of said oligomer.

14. A hydrogel comprising the reaction product of:

a) at least one oxidized polysaccharide containing aldehyde groups, having a weight-average molecular weight of about 1,000 to about 1,000,000 Daltons, said oxidized polysaccharide having an equivalent weight per aldehyde group of about 65 to about 1500 Daltons;

b) at least one water-dispersible, multi-arm polyether amine wherein at least three of the arms are terminated by at least one primary amine group, said multi-arm polyether amine having a number-average molecular weight of about 450 to about 200,000 Daltons; and c) at least one oligomer of the formula:

R1-(PS)-R2 wherein:
(i) PS is a linear polymeric segment comprising ethylene oxide monomers or a combination of ethylene oxide and propylene oxide monomers, wherein said ethylene oxide monomers comprise at least 50 weight percent of said polymeric segment;
(ii) R1 is at least one nucleophilic group capable of reacting with aldehyde groups to form at least one reversible covalent bond;
(iii) R2 is at least one functional group which is not capable of reacting with an aldehyde, a primary amine, a secondary amine, or R1 to form a covalent bond, such that said oligomer does not induce gelation when mixed in an aqueous medium with either (a) alone or (b) alone;
(iv) said oligomer has a weight-average molecular weight of about 200 to about 10,000 Daltons; and
(v) said oligomer is water soluble; and wherein said hydrogel has a decreased degradation time compared to a hydrogel formed under the same conditions in the absence of said oligomer.

15. A method for applying a hydrogel coating to an anatomical site on tissue of a living organism comprising:

applying to the site
a) at least one oxidized polysaccharide containing aldehyde groups, having a weight-average molecular weight of about 1,000 to about 1,000,000 Daltons, said oxidized polysaccharide having an equivalent weight per aldehyde group of about 65 to about 1500 Daltons;

b) at least one water-dispersible, multi-arm polyether amine wherein at least three of the arms are terminated by at least one primary amine group, said multi-arm polyether amine having a number-average molecular weight of about 450 to about 200,000 Daltons; and c) at least one oligomer of the formula:

R1-(PS)-R2 wherein:
(i) PS is a linear polymeric segment comprising ethylene oxide monomers or a combination of ethylene oxide and propylene oxide monomers, wherein said ethylene oxide monomers comprise at least 50 weight percent of said polymeric segment;
(ii) R1 is at least one nucleophilic group capable of reacting with aldehyde groups to form at least one reversible covalent bond;
(iii) R2 is at least one functional group which is not capable of reacting with an aldehyde, a primary amine, a secondary amine, or R1 to form a covalent bond, such that said oligomer does not induce gelation when mixed in an aqueous medium with either (a) alone or (b) alone;
(iv) said oligomer has a weight-average molecular weight of about 200 to about 10,000 Daltons; and
(v) said oligomer is water soluble;

wherein (a), (b), and (c) are applied to the site in any order, or (a), (b), and (c) are premixed and the resulting mixture is applied to the site before the mixture completely cures; and wherein said hydrogel coating has a decreased degradation time compared to a hydrogel coating formed under the same conditions in the absence of said oligomer.

16. The method according to claim 15 wherein the oxidized polysaccharide is a component of a first aqueous solution or dispersion, the water-dispersible, multi-arm polyether amine is a component of a second aqueous solution or dispersion, and the oligomer is a component of at least one of: (i) the first aqueous solution or dispersion; (ii) the second aqueous solution or dispersion; or (iii) a third aqueous solution or dispersion.

17. The method according to claim 15 wherein the oxidized polysaccharide is selected from the group consisting of oxidized derivatives of: dextran, carboxymethyldextran, starch, agar, cellulose, hydroxyethylcellulose, carboxymethylcellulose, pullulan, inulin, levan, and hyaluronic acid.

18. The method according to claim 15 wherein the water-dispersible, multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

19. The method according to claim 15 wherein PS is a linear polymeric segment terminating with a methylene group at both ends of said segment, wherein said segment is derived from a polymer selected from the group consisting of: polyethylene oxide, block or random copolymers of polyethylene oxide and polypropylene oxide, and tri block copolymers of polyethylene oxide and polypropylene oxide.

20. A method for decreasing the degradation time of a hydrogel formed from at least one oxidized polysaccharide (component A) and at least one water-dispersible, multi-arm polyether amine (component B), said at least one oxidized polysaccharide containing aldehyde groups, having a weight-average molecular weight of about 1,000 to about 1,000,000 Daltons and an equivalent weight per aldehyde group of about 65 to about 1500 Daltons, and said at least one water-dispersible, multi-arm polyether amine wherein at least three of its arms terminated by at least one primary amine group, said multi-arm polyether amine having a number-average molecular weight of about 450 to about 200,000 Daltons; said method comprising the step of: contacting component A and component B in the presence of an aqueous medium and at least one oligomer of the formula:

R1-(PS)-R2 wherein:
i) PS is a linear polymeric segment comprising ethylene oxide monomers or a combination of ethylene oxide and propylene oxide monomers, wherein said ethylene oxide monomers comprise at least 50 weight percent of said polymeric segment;
(ii) R1 is at least one nucleophilic group capable of reacting with aldehyde groups to form at least one reversible covalent bond;
(iii) R2 is at least one functional group which is not capable of reacting with an aldehyde, a primary amine, a secondary amine, or R1 to form a covalent bond, such that said oligomer does not induce gelation when mixed in an aqueous medium with either component A alone or component B alone;
(iv) said oligomer has a weight-average molecular weight of about 200 to about 10,000 Daltons; and
(v) said oligomer is water soluble;

wherein, in said method the oligomer is used in an amount sufficient to decrease the degradation time of the resulting hydrogel under predetermined conditions by at least 10% compared to that of the hydrogel formed under said predetermined conditions, but in the absence of said oligomer.

* * * * *